United States Patent
Qing et al.

(10) Patent No.: US 11,634,702 B2
(45) Date of Patent: Apr. 25, 2023

(54) CELL SIGNALING PATHWAY ACTIVATION BY LOCAL AC ELECTRIC FIELD

(71) Applicants: ARIZONA BOARD OF REGENTS ON BEHALF OF ARIZONA STATE UNIVERSITY, Scottsdale, AZ (US); THE REGENTS OF THE UNIVERSITY OF CALIFORNIA, Oakland, CA (US)

(72) Inventors: Quan Qing, Chandler, AZ (US); John Albeck, Davis, CA (US); Liang Guo, Davis, CA (US); Min Zhao, Davis, CA (US); Houpu Li, Tempe, AZ (US)

(73) Assignees: Arizona Board of Regents on behalf of Arizona State University, Scottsdale, AZ (US); The Regents of the University of California, Oakland, CA (US)

(*) Notice: Subject to any disclaimer, the term of this patent is extended or adjusted under 35 U.S.C. 154(b) by 391 days.

(21) Appl. No.: 16/675,127

(22) Filed: Nov. 5, 2019

(65) Prior Publication Data
US 2020/0140845 A1    May 7, 2020

Related U.S. Application Data

(60) Provisional application No. 62/756,342, filed on Nov. 6, 2018.

(51) Int. Cl.
*C12N 13/00*    (2006.01)
(52) U.S. Cl.
CPC .................................. *C12N 13/00* (2013.01)
(58) Field of Classification Search
CPC ........................................................ C12N 13/00
See application file for complete search history.

(56) References Cited

U.S. PATENT DOCUMENTS

| | | | | |
|---|---|---|---|---|
| 7,119,023 B2 * | 10/2006 | Liaw | ................... | H01L 29/7842 |
| | | | | 257/E29.147 |
| 2009/0092989 A1 * | 4/2009 | Chang | ..................... | B03C 5/026 |
| | | | | 204/600 |
| 2015/0080784 A1 | 3/2015 | Narmoneva et al. | | |
| 2018/0280968 A1 | 10/2018 | Qing et al. | | |

FOREIGN PATENT DOCUMENTS

| | | |
|---|---|---|
| WO | 2020010029 A1 | 1/2020 |
| WO | 2020010029 A9 | 1/2020 |

OTHER PUBLICATIONS

Sohn, KM et al. Hair growth-promotion effects of different alternating current parameter settings are mediated by the activation of Wnt/beta-catenin and MAPK pathway. Experimental Dermatology. 2015. 24: 958-963. (Year: 2015).*

Zhan, Y et al. Low-frequency ac electroporation shows strong frequency dependence and yields comparable transfection results to de electroporation. Journal of Controlled Release. 2012. 160: 570-576. (Year: 2012).*

Lim, J et al. Alternating current electric fields of varying frequencies: Effects on proliferation and differentiation of porcine neural progenitor cells. Cellular Reprogramming. 2013. 15(5): 405-412. (Year: 2013).*

Merrill, DR et al. Electrical stimulation of excitable tissue: design of efficacious and safe protocols. Journal of Neuroscience Methods. 2005. 141: 171-198. (Year: 2005).*

Albeck, John G., et al., "Frequency-Modulated Pulses of ERK Activity Transmit Quantitative Proliferation Signals", Molecular Cell 49, Jan. 24, 2013 [available online Dec. 2012], pp. 249-261, <https://doi.org/10.1016/j.molcel.2012.11.002>.

Allan, Lindsey A. et al., "Inhibition of caspase-9 through phosphorylation at Thr 125 by ERK MAPK", Nature Cell Biology, vol. 5, No. , Jul. 2003, pp. 647-655.

Banks, Alexander S et al., "An ERK/Cdk5 axis controls the diabetogenic actions of PPAR gamma", Nature, vol. 57, Jan. 15, 2015 [available online Nov. 17, 2014], 15 pages, <doi:10.1038/nature13887>.

Clausell, Mathis et al., "In Vivo Study of Transepithelial Potential Different (TEPD) in Proximal Convoluted Tubules of Rat Kidney by Synchronization Modulation Electric Field", J. Membrane Biol. 247(7), 2014, pp. 601-609, <DOI:10.1007/s00232-014-9676-6>.

De la Cova, Claire et al., "A Real-Time Biosensor for ERK Activity Reveals Signaling Dynamics during C. elegans Cell Fate Specification", Developmental Cell 42, Sep. 11, 2017, pp. 542-553, <http://dx.doi.org/10.1016/j.devcel.2017.07.014>.

Feng, J. et al., "Electrical Guidance of Human Stem Cells in the Rat Brain", Stem Cell Reports, Jul. 2017 [available online Jun. 2017], vol. 9, No. 1, pp. 177-189, <DOI:10.1016/j.stemcr.2017.05.035>.

Funk, R. et al., "Effects of Electromagnetic Fields on Cells: Physiological and Therapeutical Approaches and Molecular Mechanisms of Interaction: A Review", Cells Tissues Organs, Jun. 2006, vol. 182, No. 2, pp. 59-78, <DOI:10.1159/000093061>.

Hiratsuka, Toru, "Intercellular propagation of extracellular signal-regulated kinase activation revealed by in vivo imaging of mouse skin", eLife, Feb. 10, 2015, 18 pages, <DOI:10.7554/eLife.05178>.

Jura, Natalia et al., "Mechanism for Activation of the EGF Receptor Catalytic Domain by the Juxtamembrane Segment", Cell 137, Jun. 26, 2009, pp. 1293-1307, <DOI 10.1016/j.cell.2009.04.025>.

Klemke, Richard L. et al., "Regulation of Cell Motility by Mitogen-activated Protein Kinase", The Journal of Cell Biology, vol. 137, No. 2, Apr. 21, 1997, pp. 481-492.

Lai, Chung-Fang et al., "Erk Is Essential for Growth, Differentiation, Integrin Expression, and Cell Function in Human Osteoblastic Cell", The Journal of Biological Chemistry, vol. 276, No. 17, Apr. 27, 2001, pp. 14443-14450.

(Continued)

*Primary Examiner* — Renee Claytor
*Assistant Examiner* — Susan E. Fernandez
(74) *Attorney, Agent, or Firm* — Lewis Roca Rothgerber Christie LLP

(57) ABSTRACT

A method for activating a cell-signaling pathway of interest in a cell, including applying a time-modulated localized alternating current electrical field to the cell, wherein the amplitude and frequency of the localized alternating current electrical field is selected to activate the cell signaling pathway of interest, thereby activating the cell signaling pathway.

20 Claims, 22 Drawing Sheets

(56) References Cited

OTHER PUBLICATIONS

Levin, Michael et al., "Regulation of Cell Behavior and Tissue Patterning by Bioelectrical Signals: Challenges and Opportunities for Biomedical Engineering", Annual Review of Biomedical Engineering, 2012, pp. 295-323, <doi:10.1146/annurev-bioeng-071811-150114>.

Lu, Hezhe et al., "PAK signalling drives acquired drug resistance to MAPK inhibitors in BRAF-mutant melanomas", Nature, vol. 550, Oct. 5, 2017, 20 pages, <doi:10.1038/nature24040>.

Luciano, Frederic et al., "Phosphorylation of Bim-EL by Erk½ on serine 69 promotes its degradation via the proteasome pathway and regulates its proapoptotic function", Oncogene 22, 2003, pp. 6785-6793.

McKay, MM et al., "Integrating signals from RTKs to ERK/MAPK", Oncogene 26, 2007, pp. 3113-3121.

McLaughlin, Stuart et al., "An Electrostatic Engine Model for Autoinhibition and Activation of the Epidermal Growth Factor Receptor (EGFR/ErbB) Family", The Journal of General Physiology, vol. 126, No. 1, Jul. 225, pp. 41-53, <http://www.jgp.org/cgi/doi/10.1085/jgp.200509274>.

Modjtahedi, Helmout et al., "A comprehensive review of the preclinical efficacy profile of the ErbB family blocker afatinib in cancer", Naunyn-Schmiedeberg's Arch Pharmacol, 2014, pp. 505-521, <DOI 10.1007/s00210-014-0967-3>.

Monache, S. et al., "Extremely low frequency electromagnetic fields (ELF-EMFs) induce in vitro angiogenesis process in human endothelial cells", Bio Electro Magnetics, Dec. 2008 [available online May 2008], vol. 29, No. 8, pp. 640-648, <DOI:10.1002/bem.20430>.

Morotomi-Yano, Keiko et al., "Nanosecond pulsed electric fields activate MAPK pathways in human cells", Archives of Biochemistry and Biophysics 515, Sep. 10, 2011, pp. 99-106, <doi:10.1016/j.abb.2011.09.002>.

Murphy, Leon O. et al., "Molecular interpretation of ERK signal duration by immediate early gene products", Nature Cell Biology, vol. 4, Aug. 2002, 12 pages, <DOI:10.1038/ncb822>.

Nie. K. et al., "MAP kinase activation in cells exposed to a 60 Hz electromagnetic field", Journal of Cellular Biochemistry, Dec. 2003 [available online Nov. 2003], vol. 90. No. 6, pp. 1197-1206, <DOI:10.1002/cb.10704>.

Oda, Kanae et al., "A comprehensive pathway map of epidermal growth factor receptor signaling", Molecular Systems Biology, 2005, 17 pages, <doi:10 1038/msb4100014>.

Regot, Sergi et al., "High-Sensitivity Measurements of Multiple Kinase Activities in Live Single Cells", Cell 157, Jun. 19, 2014, pp. 1724-1734, <http://dx.doi.org/10.1016/j.cell.2014.04.039>.

Rodland, Karin D. et al., "Multiple Mechanisms Are Responsible for Transactivation of the Epidermal Growth Factor Receptor in Mammary Epithelial Cells", The Journal of Biological Chemistry, vol. 283, No. 46, Nov. 14, 2008 [available online Sep. 2008], pp. 31477-31487, <DOI 10.1074/jbc.M800456200>.

Roux, Philippe P et al., "ERK and p38 MAPK-Activated Protein Kinases: a Family of Protein Kinases with Diverse Biological Functions", Microbiology and Molecular Biology Reviews, vol. 68, No. 2, Jun. 2004, pp. 320-344, <DOI: 10.1128/MMBR.68.2.320-344.2004>.

Ryu, Hyunryul et al., "Frequency modulation of ERK activation dynamics rewires cell fate", Molecular Systems Biology 11, 2015, 14 pages, <DOI 10.15252/msb.20156458>.

Semenov, Iurii et al., "Primary pathways of intracellular Ca2+ mobilization by nanosecond pulsed electric field", Biochimica et Biophysica Acta 1828, 2013, pp. 981-989, <http://dx.doi.org/10.1016/j.bbamem.2012.11.032>.

Shankaran, Harish et al., "Rapid and sustained nuclear-cytoplasmic ERK oscillations induced by epidermal growth factor", Molecular Systems Biology 5, Article No. 332, 2009, 13 pages, <doi:10.1038/msb.2009.90>.

Sheikh, A. et al., "Regulation of endothelial MAPK/ERK signalling and capillary morphogenesis by low-amplitude electric field", Journal of the Royal Society, Jan. 2013, vol. 10, No. 78, article 20120548, 13 pages, <DOI:10.1098/rsif.2012.0548>.

Sparta, Breanne et al., "Receptor Level Mechanisms Are Required for Epidermal Growth Factor (EGF)-stimulated Extracellular Signal-regulated Kinase (ERK) Activity Pulses", The Journal of Biological Chemistry, vol. 290, No. 41, Oct. 9, 2015 [available online Aug. 2015], pp. 24784-24792, <DOI:10.1074/jbc.M115.662247>.

Stork, Philip J.S., "Erk Signaling: Duration, Duration, Duration", Cell Cycle, vol. 1, Issue 5, Sep./Oct. 2002, pp. 315-317.

Subramaniam, Srinivasa et al., "ERK activation promotes neuronal degeneration predominantly through plasma membrane damage and independently of caspase-3", The Journal of Cell Biology, vol. 165, No. 3, May 10, 2004, pp. 357-369, <http://www.jcb.org/cgi/doi/10.1083/jcb.200403028>.

Taghian T. et al., "Modulation of cell function by electric field: a high-resolution analysis", J. R. Soc. Interface 12, 2015, 11 pages, <http://dx.doi.org/10.1098/rsif.2015.0153>.

Toettcher, Jared E. et al., "Using Optogenetics to Interrogate the Dynamic Control of Signal Transmission by the Ras/Erk Module", Cell 155, Dec. 5, 2013, pp. 1422-1434, <http://dx.doi.org/10.1016/j.cell.2013.11.004>.

Tran, V. et al., "Synchronization modulation increases transepithelial potentials in MDCK monolayers through Na/K pumps", PloS One, Apr. 2013, vol. 8, No. 4, article e61509, 9 pages, <DOI:10.1371/journal.pone.006150>.

Von Kriegsheim, Alex et al., "Cell fate decisions are specified by the dynamic ERK interactome", Nature Cell Biology, vol. 11, No. 12, Dec. 2009 [available online Nov. 2009], 22 pages, <DOI:10.1038/ncb1994>.

Wang, E. et al., "Electric Fields and MAP Kinase Signaling Can Regulate Early Wound Healing in Lens Epithelium", Investigative Ophthalmology & Visual Science, Jan. 2003, vol. 44, No. 1, pp. 244-249, <DOI:10.1167/ovs.02-0456>.

Wolf-Goldberg, Tami et al., "Low electric fields induce ligand-independent activation of EGF receptor and ERK via electrochemical elevation of H+ and ROS concentrations", Biochimica et Biophysica Acta 1833, 2013 [available online Feb. 2013], pp. 1396-1408, <http://dx.doi.org/10.1016/j.bbamcr.2013.02.011>.

Wortzel, Inbal et al., "The ERK Cascade: Distinct Functions within Various Subcellular Organelles", Genes & Cancer, vol. 2, No. 3, 2011, pp. 195-209, <DOI:10.1177/1947601911407328>.

Yao, Jing et al., "Rapid Temperature Jump by Infrared Diode Laser Irradiation for Patch-Clamp Studies", Biophysical Journal, vol. 96, May 2009, pp. 3611-3619, <doi:10.1016/j.bpj.2009.02.016>.

Zhao, M. et al., "Membrane lipids, EGF receptors, and intracellular signals colocalize and are polarized in epithelial cells moving directionally in a physiological electric field", The FASEB Journal, Jun. 2002 [available online Apr. 2002], vol. 16, No. 8, pp. 857-859, <DOI:10.1096/fj.01-0811fje>.

* cited by examiner

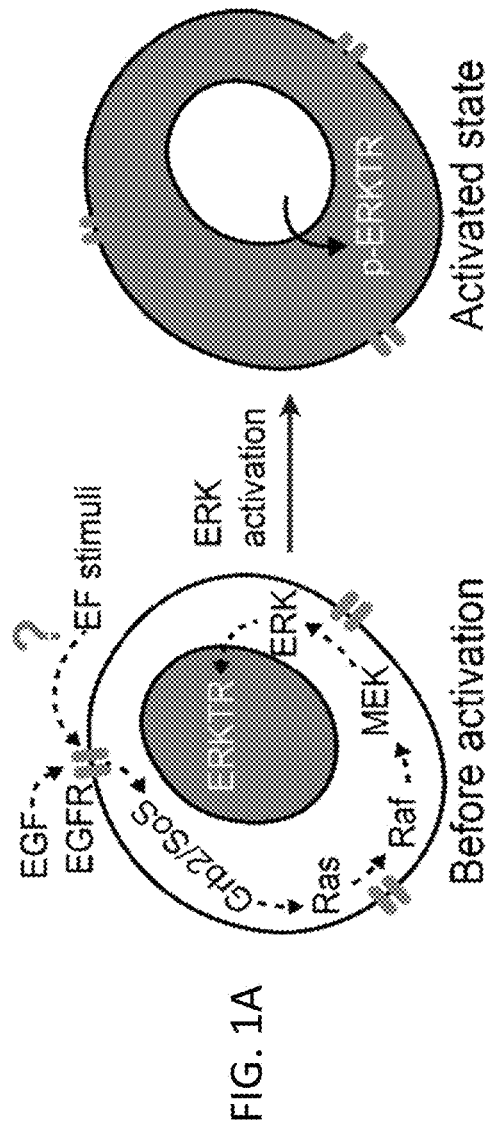
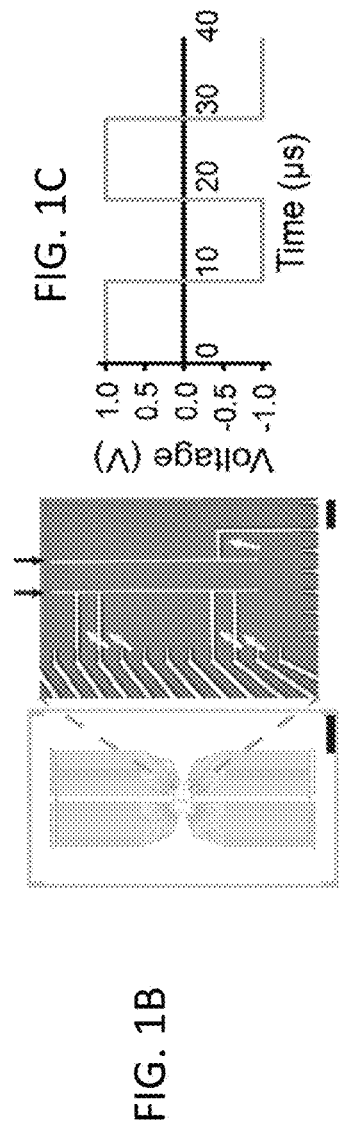
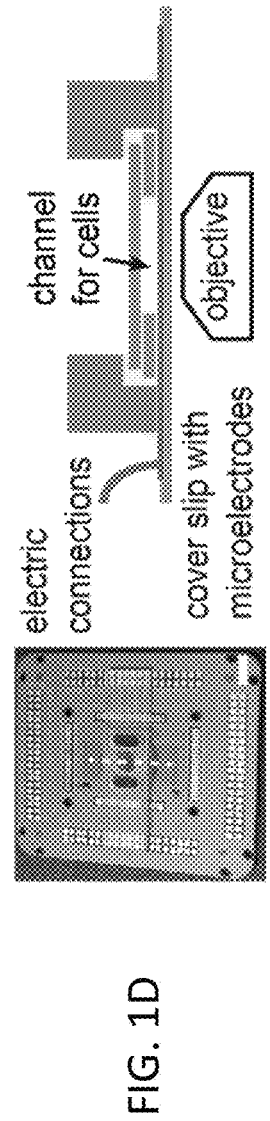
FIG. 1A
FIG. 1B
FIG. 1C
FIG. 1D

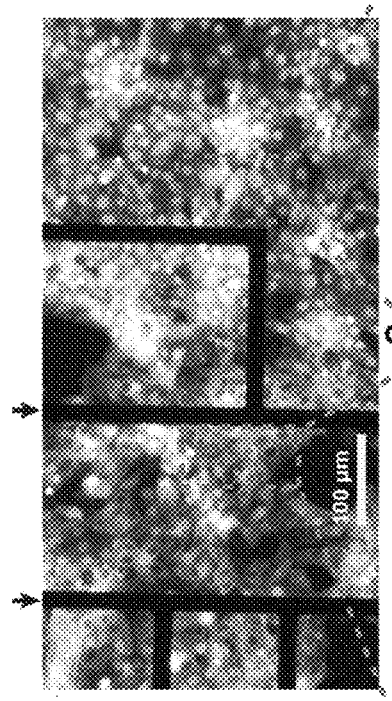
FIG. 2A
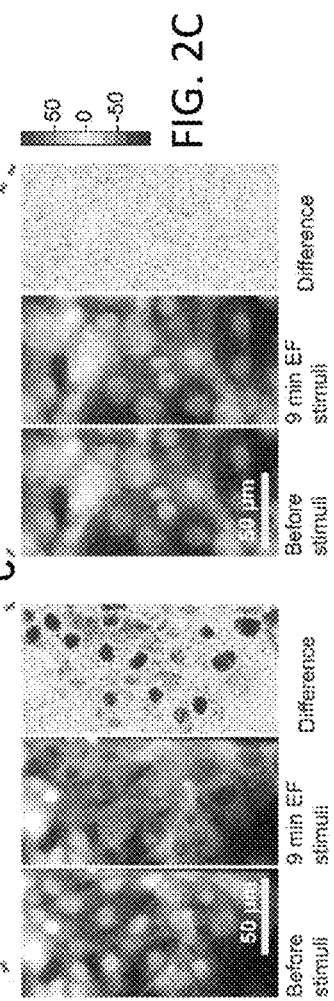
FIG. 2B
FIG. 2C
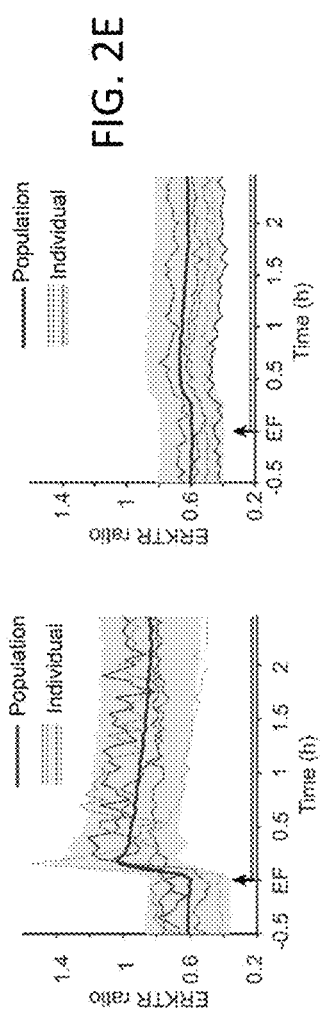
FIG. 2D
FIG. 2E

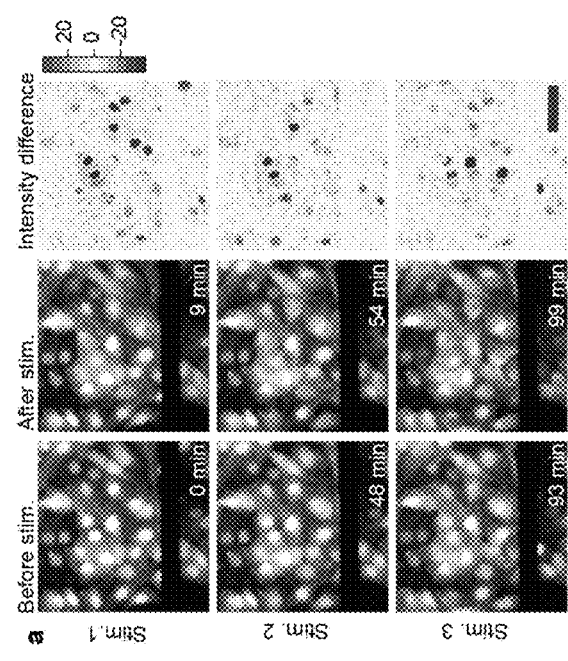
FIG. 4A
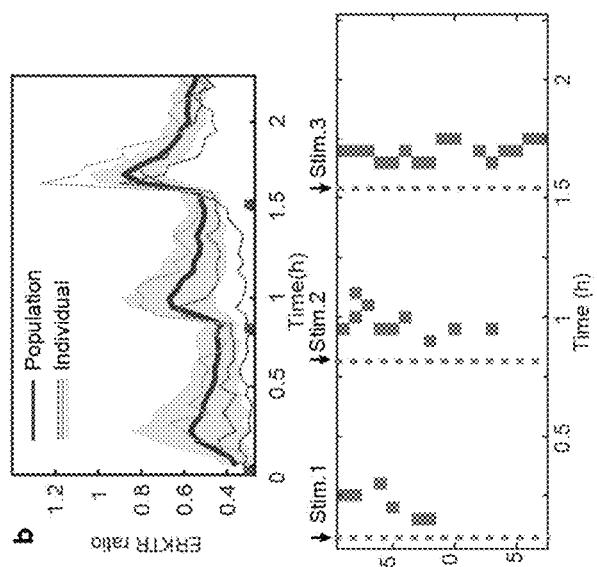
FIG. 4B
FIG. 4C

FIG. 5A
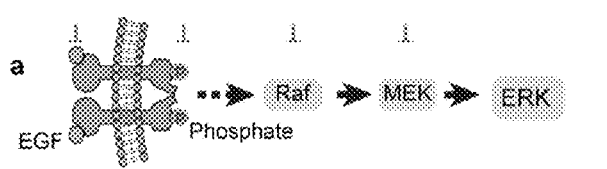
FIG. 5B
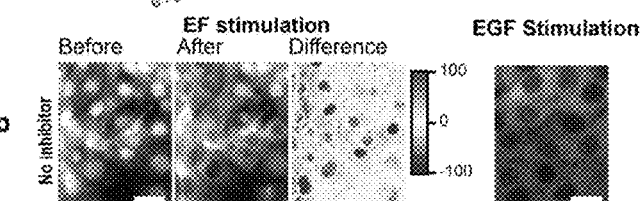
FIG. 5C
FIG. 5D
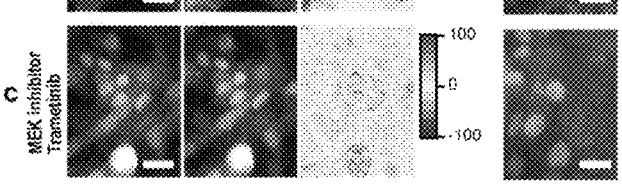
FIG. 5E
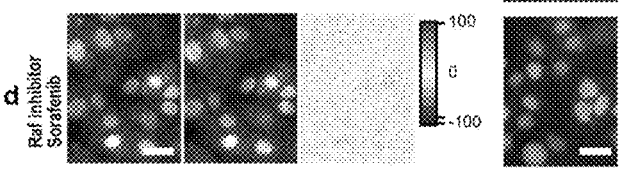
FIG. 5F
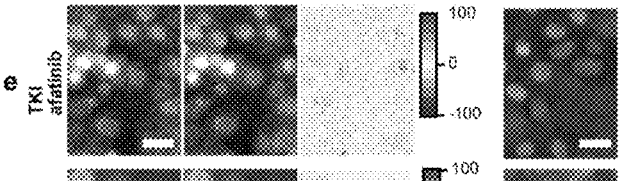
FIG. 5G
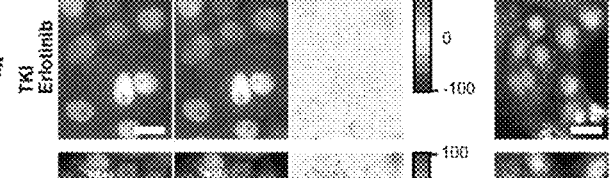
FIG. 5H
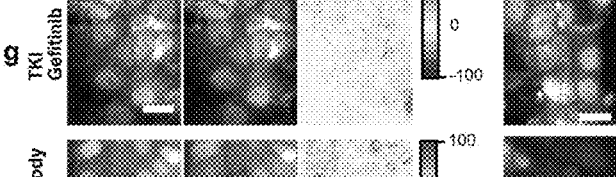
FIG. 5I
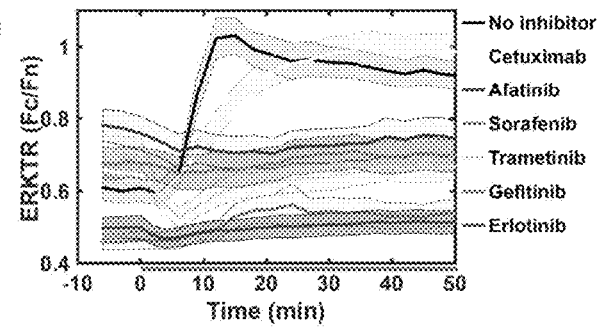

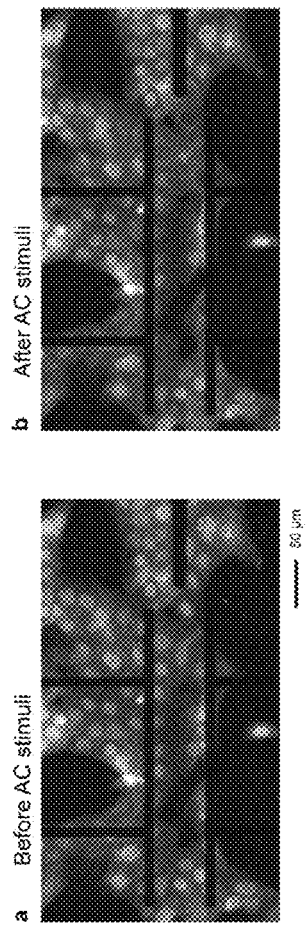
FIG. 11A
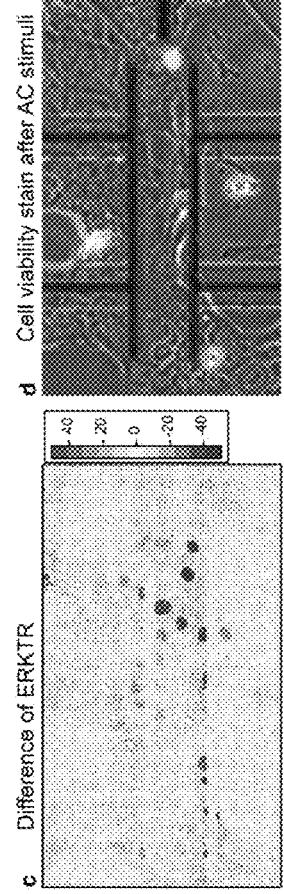
FIG. 11B
FIG. 11C
FIG. 11D
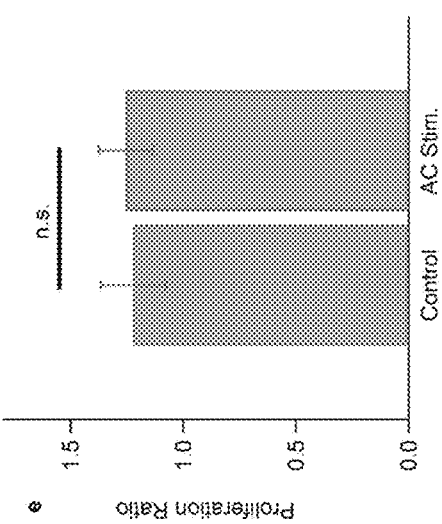
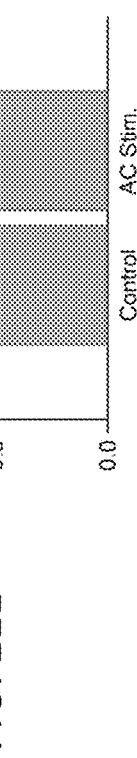
FIG. 11E

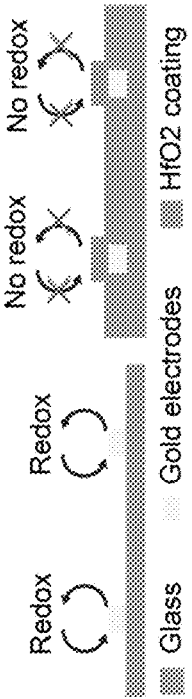
FIG. 12A
FIG. 12B
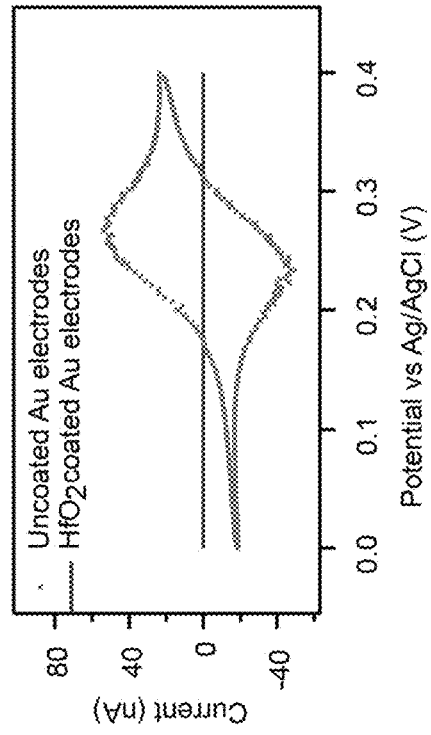
FIG. 12C
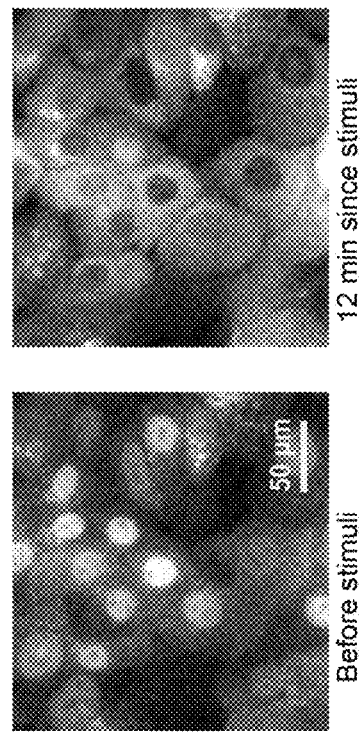
FIG. 12D a 37 °C b 38 °C c 39 °C d 35 °C

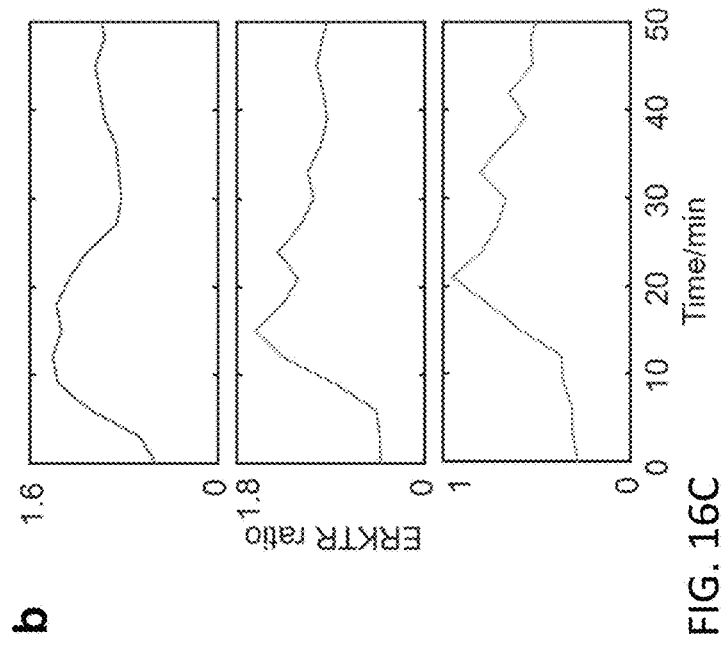
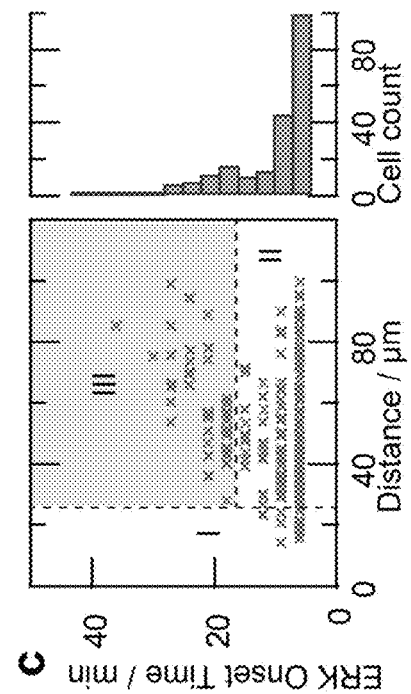
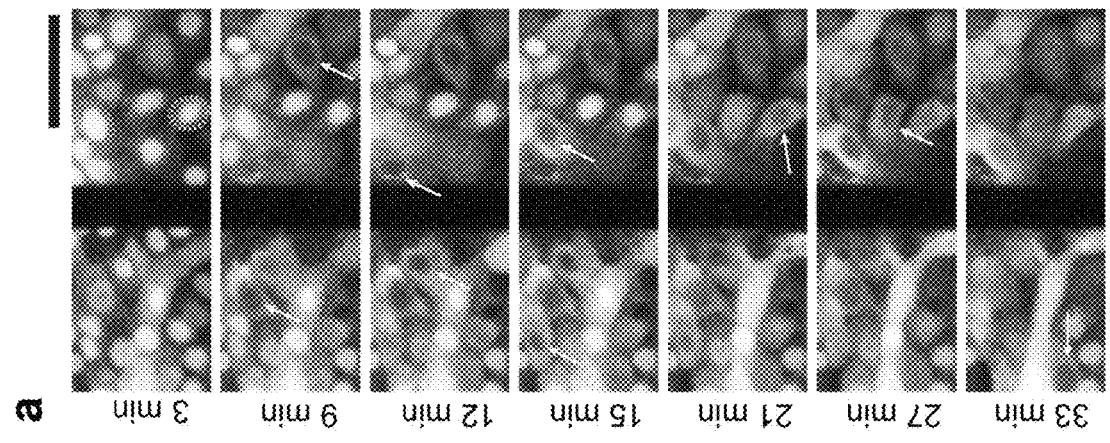
FIG. 16A
FIG. 16B
FIG. 16C

US 11,634,702 B2

CELL SIGNALING PATHWAY ACTIVATION BY LOCAL AC ELECTRIC FIELD

CROSS-REFERENCE TO RELATED APPLICATION

This application claims the priority benefit of the earlier filing of U.S. Provisional Application No. 62/756,342, filed Nov. 6, 2018, which is specifically incorporated herein by reference in its entirety.

ACKNOWLEDGEMENT OF GOVERNMENT SUPPORT

This invention was made with government support under FA9550-16-1-0052 awarded by the Air Force Office of Scientific Research and R21 EB020822, R21 EB015737, and R01 EY019101 awarded by the National Institutes of Health. The government has certain rights in the invention.

FIELD

This disclosure relates to methods of modulating cell signaling pathways, and specifically, the application of electric fields to modulate the activity of protein kinases, such as extracellular-signal-regulated kinase (ERK).

BACKGROUND

Cell signaling is part of any communication process that governs basic activities of cells and coordinates all cell actions. The ability of cells to perceive and correctly respond to their microenvironment is the basis of development, tissue repair, and immunity, as well as normal tissue homeostasis. In many instances, dysregulated or aberrant cell signaling, such as from kinases, can lead to diseases, such as cancer, autoimmunity, and diabetes.

In some cases, receptor activation caused by ligand binding to a receptor is directly coupled to the cell's response to the ligand. However, for many cell surface receptors, ligand-receptor interactions are not directly linked to the cell's response. The activated receptor must first interact with other proteins inside the cell before the ultimate physiological effect of the ligand on the cell's behavior is produced. Often, the behavior of a chain of several interacting cell proteins is altered following receptor activation. The entire set of cell changes induced by receptor activation is called a signal transduction mechanism or pathway. Several of these receptors are kinases that start to phosphorylate themselves and other proteins when binding to a ligand. Phosphorylation can generate a binding site for a different protein and thus induce protein-protein interaction. Complex multicomponent signal transduction pathways provide opportunities for feedback, signal amplification, and interactions inside one cell between multiple signals and signaling pathways. The ability to modulate cell signaling could lead to more effective treatments as well as creation of artificial tissues.

BRIEF DESCRIPTION OF THE DRAWINGS

FIGS. 1A-1D The reporter cell and chip design (FIG. 1A) A schematic of ERK translocation reporter (ERKTR, pink color) translocate from the nucleus to cytosol upon activation of EGFR-Ras-ERK signaling pathway (FIG. 1B) Left: The overall of the microelectrode arrays on the glass cover slip. Right: An optical image of one pair of microelectrodes at the center of the chip. The white arrows mark the metal connections that are passivated by 500 nm thick SU-8 polymer. The black arrows mark the exposed parallel microelectrodes. Scale bars, left: 5 mm, right: 200 µm. (FIG. 1C) The waveform of the bipolar electric pulses applied to the electrodes (FIG. 1D) Left: A photo of the assembled cell chamber on the chip and printed circuit board (PCB) Scale bar 10 mm. The yellow dash line marks the position of the cross-section shown on the right. Right: Schematics of the cross-section structure of the chamber.

FIGS. 2A-2E. Localized ERK activation by AC EF. (FIG. 2A) AC EF induced localized ERK activation between a pair of microelectrode bars (marked by the arrows). (FIG. 2B and FIG. 2C) Cells between the microelectrodes (FIG. 2B) and in an adjacent area (FIG. 2C) before and after onset of stimulation. The color-coded images on the right of each panel show the difference of fluorescence intensity before and after stimulation Blue and orange colors mark areas where the fluorescence intensity decrease and increase respectively. (FIG. 2D) Time traces of ERKTR ratio of individual representative cells and population average from 164 cells within 100 µm from the electrode. Average data are presented as mean (thick blue line)±SD (light shadow) Black arrow denotes the time of applying AC-EF and red line indicate the sustained EF stimuli. (FIG. 2E) Time traces of ERKTR ratio of individual representative cells and population average from 160 cells within the region of 200 to 700 µm away from the electrode. Data are presented as mean (thick blue line)±SD (light shadow). Black arrow denotes the time of applying AC-EF and red line indicate the sustained EF stimuli.

(FIG. 3A) Three cells showing oscillation of ERK under continuous AC EF stimulation. Fluorescent images taken at 0, 10, 20, 30, 40, 50 and 60 minute as continuous AC EF stimuli were applied. Cells circled in orange, blue, and green all demonstrated repeated pulsatile ERK activation. Scale bar: 20 µm. (FIG. 3B) Time traces of the ERKTR ratio of the three cells in (FIG. 3A), peaks (ERK active) and valleys (ERK at rest) were identified. The black arrow denotes the start time of EF stimulation and red line marks the sustained EF stimuli. (FIG. 3C) Peak time map of the 164 cells in FIG. 2D under sustained AC EF stimulation. 35 cells showed multiple peaks (>=2) in 3 hours. The black dashed line indicated the time of exposure to AC EF stimulation.

FIGS. 4A-4C. Repeated short AC-EF stimulation induced synchronized ERK activation. (FIG. 4A) Fluorescent images of cells before (left) and after (middle) the 3-minute long AC EF stimulations started at 0, 48 and 93 min. Right: Color coded intensity difference. Blue and orange colors mark areas where the fluorescence intensity decreased and increased, respectively. Scale bar: 50 µm. (FIG. 4B) Time traces of ERKTR ratio from individual representative cells and population average from 17 cells. The short red lines mark the duration of EF stimuli. Data are presented as mean (thick blue line)±SD (light shadow). (FIG. 4C) Peak time map of ERK activities.

FIGS. 5A-5I. Blocker tests following the EGFR-Raf-ERK signaling pathway. (FIG. 5A) Schematics of the EGF-Ras-ERK signaling pathway and the blocked sites, including the extracellular EGF binding site, the intracellular phosphorylation site of EGFR, Raf and MEK. (FIGS. 5B-5H) (Images on the left group) Fluorescence images of cells before and after AC EF stimulation, and the intensity difference; and (Images on the right group) fluorescence images of control groups stimulated by EGF chemical stimulation (2 ng/mL), when no inhibitors were applied (FIG. 5B), and with MEK inhibitor trametinib (0.5 µM) (FIG. 5C), Raf inhibitor sorafenib (20 µM) (FIG. 5D), tyrosine kinase inhibitors afatinib (5 µM) (FIG. 5E), erlotinib (2 µM) (FIG. 5F), gefitinib (50 µM) (FIG. 5G), and EGFR binding-site antibody cetuximab (100 µg/mL) (FIG. 5H), respectively. Scale bars: 25 µm. (FIG. 5I) Time traces of ERKTR ratio as population average from cells under AC EF stimulations in (FIGS. 5B-5H). Mean and ±95% CI are shown as a solid line and shadow region, respectively (n>100 cells for each group).

(FIG. 6A) Cyclic voltammetry scan of gold microelectrode in culture media DMFM/F-12(Cat #21041025, Life Technologies) with two electrodes configuration, scan rate 25 mV/s. (FIG. 6B) Optical microscope image of gold electrode before and after bipolar 10 µs wide±1.5V EF pulses were continuously applied for >1 hour.

(FIG. 7A) Simulation of the electric field at the cross section of the microelectrode pair when an alternating current (AC) voltage with an amplitude of 1V and frequency of 50 kHz is applied on one of the electrode and the ground is connected to the other electrode. (FIG. 7B) Simulation of electric field value on the line between two centers of electrodes on the substrate surface and the nominal field is about 8.2 V/cm at the 100 away from the electrode, while the electric field at the edge of the electrode is about 24 V/cm.

(FIG. 8A) Heat map plot summarizing the ERKTR ratio of cells close to the electrodes in FIG. 2D. Warmer color indicates higher ratio and higher level of ERK activity. Continuous AC-EF stimulation starts at the time of dashed line and red line indicate the sustained EF stimuli. (FIG. 8B) Heat map plot summarizing the ERKTR ratio of cells far away from the electrodes in FIG. 2E. Warmer color indicates higher ratio and higher level of ERK activity. Continuous AC-EF stimulation starts at the time of dashed line and red line indicate the sustained EF stimuli.

FIGS. 11A-11E. Cell viability staining test. (FIG. 11A) Fluorescence image of cell before EF stimuli was applied. (FIG. 11B) Fluorescence image of cell after EF stimuli was applied. (FIG. 11C) Difference of ERKTR reporter in A and B, blue indicates ERKTR intensity drop. (FIG. 11D) Phase contrast and fluorescence staining image after 2 hours of EF stimuli was applied. Blue staining that are membrane permeable indicates alive cells, while dead cells are labelled with green dye. (FIG. 11E) Cell proliferation rate comparison. p>0.05 (n=4).

FIGS. 12A-12D. ERK activation using $HfO_2$ coating electrodes. (FIG. 12A) Redox reactions can happen on bare metal electrode surface. (FIG. 12B) The redox reactions are suppressed by the insulating $HfO_2$ coating. (FIG. 12C) Cyclic voltammetry scan in 5 mM ferrocyanide/ferricyanide solution of microelectrodes with (blue line) and without (red line) HfO2 coating, tested with 0.1 M KCl as support electrolyte at sweeping rate of 50 mV/s. (FIG. 12D) Activation of ERK by AC EF through electrodes with HfO2 coating.

(FIG. 15A) Cells incubated at 37° C. (FIG. 15B) Cells exposed to 38° C. for 10 min. (FIG. 15C) Cells exposed to 39° C. for 10 min. (FIG. 15D) Cells exposed to 35° C. for 10 min.

FIGS. 16A-16C. Onset time of ERK response for cells at different distances from the electrodes. (FIG. 16A) Fluorescence images showing the time sequence of cell activations. The yellow arrows mark the position of newly activated cells from the previous frames. The circles in red, green and blue mark the cells that are used for the time traces in (FIG. 16B), which are 25, 41 and 47 µm away from the electrode, respectively. Scale bar: 50 µm. (FIG. 16B) Time traces of the ERKTR ratio for the cells circled in red, green, and blue in (FIG. 16A), respectively, from which the onset time can be determined as 6, 9 and 15 minutes, respectively. (FIG. 16C) Left: ERK activation onset time of all 216 cells vs distance within 100 µm from the electrodes. Region I: Cells that were within 25 µm from the electrodes were all activated within 10 minutes; Region II: ~77% of the cells that are >30 µm away from the electrodes showed a distance-independent short response time (<=15 minutes); Region III: ~23% of the cells that are >30 µm away from the electrodes demonstrated longer onset time with random distribution. Right: Histogram of ERK activation onset time.

(FIG. 17B) Waveform of the AC EF pulses for each 3-minute long stimulation.

(FIG. 20A) Cross-membrane potential estimated assuming EF=10 V/cm in the medium. (FIG. 20B) Capacitive impedance of the electrodes at different frequencies, assuming a geometry of the electrodes as 10 µm in width, 200 µm in length, and the distance between electrodes as 100 µm. (FIG. 20C) Cross-membrane potential estimated taking into consideration of the impedance change of the electrodes at different frequencies, assuming the same peak-to-peak potential is applied.

(FIG. 21A) Before AC stimuli is delivered. (FIG. 21B) 15 min after AC EF stimulation. (FIG. 21C) Difference of ERKTR reporter, calculated by subtraction of B and A.

DETAILED DESCRIPTION OF SEVERAL EMBODIMENTS

Figure 3A:
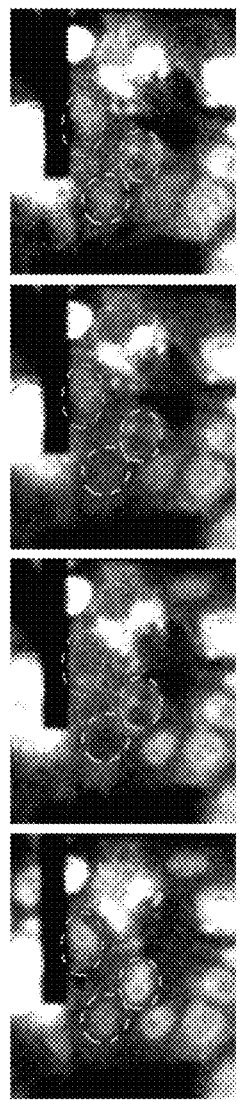
FIGS. 3A-3C. ERK oscillations under sustained AC EF stimulation.
Figure 3A:
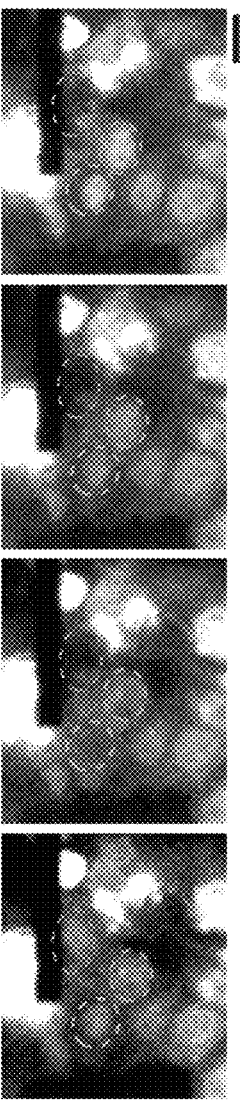

Unless otherwise noted, technical terms are used according to conventional usage. Definitions of common terms in molecular biology may be found in Benjamin Lewin, Genes V, published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCR Publishers, Inc., 1995 (ISBN 1-56081-569-8).

Unless otherwise explained, all technical and scientific terms used herein have the same meaning as commonly understood by one of ordinary skill in the art to which this disclosure belongs. Although methods and materials similar or equivalent to those described herein can be used in the practice or testing of this disclosure, suitable methods and materials are described below. In addition, the materials, methods, and examples are illustrative only and not intended to be limiting.

The following explanations of terms and methods are provided to better describe the present compounds, compositions and methods, and to guide those of ordinary skill in the art in the practice of the present disclosure. It is also to be understood that the terminology used in the disclosure is for the purpose of describing particular embodiments and examples only and is not intended to be limiting.

As used herein, the singular forms "a," "an," and "the" are intended to include the plural forms as well, unless the context clearly indicates otherwise.

As used herein, the term "and/or" refers to and encompasses any and all possible combinations of one or more of the associated listed items, as well as the lack of combinations when interpreted in the alternative ("or").

As used herein, "one or more" or at least one can mean one, two, three, four, five, six, seven, eight, nine, ten or more, up to any number.

As used herein, the term "comprises" means "includes." Hence "comprising A or B" means including A, B, or A and B.

The term "a cell" as used herein includes a single cell as well as a plurality or population of cells.

Cell signaling pathway: In cell biology, there are several signaling pathways. Cell signaling is part of the molecular biology system that controls and coordinates the actions of cells. Cell signaling pathways include, but are not limited to the following: Akt/PKB signaling pathway; AMPK signaling pathway; cAMP-dependent pathway; Hedgehog signaling pathway; Hippo signaling pathway; insulin signal transduction pathway; JAK-STAT signaling pathway; MAPK/ERK signaling pathway; mTOR signaling pathway; Nodal signaling pathway; Notch signaling pathway; PI3K/AKT/mTOR signaling pathway; TGF beta signaling pathway; TLR signaling pathway; VEGF signaling pathway; and the Wnt signaling pathway.

The ERK1/2 pathway of mammals is probably the best-characterized MAPK system. The most important upstream activators of this pathway are the Raf proteins (A-Raf, B-Raf or c-Raf), the key mediators of response to growth factors (EGF, FGF, PDGF, etc.); but other MAP3Ks such as c-Mos and Tpl2/Cot can also play the same role. All these enzymes phosphorylate and thus activate the MKK1 and/or MKK2 kinases, that are highly specific activators for ERK1 and ERK2. The latter phosphorylate a number of substrates important for cell proliferation, cell cycle progression, cell division and differentiation (RSK kinases, Elk-1 transcription factor, etc.).

Introduction

The ERK signaling pathway regulates critical cell behaviors, including, for example cell motility, survival, proliferation and fate determination/differentiation. Aberrant signaling of this pathway underlies many important diseases, including cancer and diabetes. Recent advances in imaging the dynamics of ERK activation with single cell resolution started to reveal critical coding mechanisms and rich information embedded there. For example, the decision to enter S phase and proliferation of mammary epithelial cells (MC10A cells) is influenced by the frequency of ERK activation. The change in ERK dynamics in PC12 cells modulated by different pulsed EGF stimulations can decide whether they proliferate or differentiate into neuron-like cells. In addition, the critical roles of ERK activation dynamics in vivo have also been demonstrated. In mouse epidermis, bursts of ERK activation propagate from cell to cell with the propagation frequency correlates with the rate of epidermal cell division. Upon injury, ERK activation propagates as waves in parallel to the wound edge and is associated with G2/M cell cycle progression. In C. elegans development, different cell fate specification shows different spatiotemporal pulse of ERK activation.

A practical method to control the frequency as well as amplitude of ERK activation will be of great value in both basic research as well as possible clinical applications, Frequency modulation (FM) of ERK activation has been achieved with optogenetics, where genetically modified light sensitive molecules are expressed in target cells and light signals are shined at controlled frequency upon cells. Another method of FM is through pulsed stimulation with EGF (epidermal growth factor), in which addition and washout of EGF is repeated at required frequency.

As disclosed herein, the inventors have developed a method of frequency modulation of ERK activation that does not require repeated addition and washout of chemicals, or genetic-modification of cells. The inventors have demonstrated that alternating current (AC) electric field (EF) stimulation can be used to induce defined FM of ERK activation. As shown in the Example below, time-modulated symmetric bipolar AC-EF of tens of kHz can directly trigger highly localized and synchronized ERK activation without Faradaic process. In addition, the inventors demonstrate highly specific AC-EF induced ligand-free EGFR phosphorylation. Amplitude, duration, and frequency of activation of the extracellular-signal-regulated kinase (ERK) pathway code diverse spectrum of information at cell, tissue and organism levels to instruct cells to migrate, proliferate, or differentiate. Synchronized frequency control of ERK activation would provide a powerful approach to regulate cell behaviors. As disclosed herein the inventors demonstrate that modulation of ERK activities using alternative current (AC) electric fields (EFs) in a new frequency range can be applied through high-k dielectric passivated microelectrodes with single-cell resolution. By modulation of both the amplitude and frequency of the AC-EF ERK activation can be precisely controlled, synchronized and modulated. As disclosed herein the ERK activation was demonstrated to be independent of Faradaic currents and electroporation, thus excluding previously suggested mechanisms of ERK activation by pH, reactive oxygen species and other electrochemical reaction. It was further demonstrated that the mechanism of phosphorylation site of EGF receptor to activate the EGFR-ERK pathway was independent of epidermal growth factor (EGF). Thus, as disclosed herein AC-EFs provide a new strategy to precisely control the dynamics of ERK activation, which serves as a powerful platform for control of cell behaviors with implications in wide range of biomedical applications.

This disclosure provides a new strategy and practical technology of precise ERK modulation with high spatial resolution and temporal control, and provides for the design of electroceuticals to regulate important biological processes and treat diverse diseases through modulation of intracellular signaling pathways. In addition the methods disclosed herein while specifically demonstrated to ERK activation can be applied to other cell signaling pathways and the modulation of other cell membrane proteins, for example by selection of the amplitude, frequency, wave shape and/or time modulation of the AC-EFs. In addition to activation of the cell signaling pathways, it is further contemplated that the disclosed methods could be used to selectively suppress cell-signaling pathways, such as by EF stimuli, by fine-tuning of the parameters discussed herein.

Aspects of the present disclosure are drawn to a method for modulating a cell signaling pathway of interest in a cell, for example, one or more of a Akt/PKB signaling pathway; a AMPK signaling pathway; a cAMP-dependent pathway; a Hedgehog signaling pathway; a Hippo signaling pathway; an Insulin signal transduction pathway; a JAK-STAT signaling pathway; a MAPK/ERK signaling pathway; a mTOR signaling pathway; a Nodal signaling pathway; a Notch signaling pathway; a PI3K/AKT/mTOR signaling pathway; a TGF beta signaling pathway; a TLR signaling pathway; a VEGF signaling pathway; and a Wnt signaling pathway. In a specific embodiment, the cell-signaling pathway of interest is the ERK pathway. In embodiments, the methods include applying a time-modulated AC-EF to the cell, wherein the amplitude and frequency of the alternating current electrical field is selected to activate the cell-signaling pathway of interest, thereby activating the cell-signaling pathway. In embodiments, the methods include selecting a shape and/or timing of the time-modulated localized AC-EF to activate the cell-signaling pathway of interest. In embodiments, the frequency of the AC-EF is between about 10 Hz to about 30 MHz, including 10 Hz, 20 Hz, 30 Hz, 40 Hz, 50 Hz, 60 Hz, 70 Hz, 80 Hz, 90 Hz, 100 Hz, 150 Hz, 200 Hz, 250 Hz, 300 Hz, 350 Hz, 400 Hz, 450 Hz, 500 Hz, 600 Hz, 700 Hz, 800 Hz, 900 Hz, 1 MHz, 2 MHz, 3 MHz, 4 MHz, 5 MHz, 7 MHz, 8 MHz, 9 MHz, 10 MHz, 20 MHz, 30 MHz. In some examples, the frequency of the AC-EF is between about 500 Hz and 5 MHz, between about 500 Hz and 1 MHz, between about 500 Hz and 10 MHz, between about 700 Hz and 2 MHz, between about 500 Hz and 4 MHZ, between about 1 MHz and 4 MHZ, or between 3 MHz and 5 MHz. In embodiments, the shape of the alternating current electrical field is selected from square wave, sine wave, triangle wave, and sawtooth wave or combinations thereof, combined with or without silence interval time between pulses. In embodiments, the timing of each pulses phase of the alternating current electrical field is between about 200 nanoseconds and about 2 milliseconds, such as 200 ns, 300 ns, 400 ns, 500 ns, 600 ns, 700 ns, 800 ns, 900 ns, 1 μs, 10 μs, 20 μs, 50 μs, 100 μs, 200 μs, 300 μs, 400 μs, 500 μs, 600 μs, 700 μs, 800 μs, 900 μs, 1 ms, 1.5 ms and 2 ms, The timing of the interval between each pulse is between 0 to 2 millisecond, such as 0.0 ms, 0.5 ms 1 ms, 1.5 ins and 2 ms. In embodiments, the AC-EF is selected so that when applied it does not cause a net ion current, nor cause electroporation of the cell membrane. In embodiments, the alternating current electrical field is delivered continuously for about 15 minutes to more than about 2 hours. In embodiments, the alternating current electrical field is delivered in repeated cycles between an active period of about 1 minute to about 30 minutes, and a silent period of about 10 minutes to about 60 minutes.

In embodiments, the amplitude of the AC bias delivered to electrodes is between about 0.1V to about 10 V, such as 0.1V, 0.2V, 0.3V, 0.4V, 0.5V, 0.6V, 0.7V, 0.8V, 0.9V, 1.0V, 1.1V, 1.2V, 1.3V, 1.4V, 1.5V, 1.6V, 1.7V, 1.8V, 1.9V, 2.0V, 2.1V, 2.2V, 2.3V, 2.4V, 2.5V, 2.6V, 2.7V, 2.8V, 2.9V, 3.0V, 3.1V, 3.2V, 3.3V, 3.4V, 3.5V, 3.6V, 3.7V, 3.8V, 3.9V, 4.0V, 4.1V, 4.2V, 4.3V, 4.4V, 4.5V, 4.6V, 4.7V, 4.8V, 4.9V, 5.0V, 5.1V, 5.2V, 5.3V, 5.4V, 5.5V, 5.6V, 5.7V, 5.8V, 5.9V, 6.0V, 6.1V, 6.2V, 6.3V, 6.4V, 6.5V, 6.6V, 6.7V, 6.8V, 6.9V, 7.0V, 7.1V, 7.2V, 7.3V, 7.4V, 7.5V, 7.6V, 7.7V, 7.8V, 7.9V, 8.0V, 8.1V, 8.2V, 8.3V, 8.4V, 8.5V, 8.6V, 8.7V, 8.8V, 8.9V, 9.0V, 9.1V, 9.2V, 9.3V, 9.4V, 9.5V, 9.6V, 9.7V, 9.8V, 9.9V, and 10V.

In embodiments, the activation results in a post translational modification of a signaling protein in the cell signaling pathway, for example phosphorylation of one or more proteins in the cell signaling pathway. In specific embodiments, the amplitude and frequency of the localized alternating current electrical field is selected to cause EGFR phosphorylation in the absence of EGF binding.

In embodiments, the electrical field is applied with surface microelectrode pairs. In embodiments, the surface of the microelectrode pairs include a surface coating to reduce the Faradic process. In embodiments, the microelectrode pairs are dielectric passivated microelectrodes. In certain embodiments, the dielectric passivation comprises high-k dielectric materials, in certain embodiments, the dielectric passivation comprises one or a combination of the following materials: $HfO_2$, $ZrO_2$, $Al_2O_3$, $SiO_2$, $TiO_2$ $Ta_2O_5$ $La_2O_3$, $Pr_2O_3$, $CrO_2$. In one embodiment, the high-k dielectric comprises $HfO_2$.

The disclosed systems, processes, methods and the like can be used to treat a subject, such as a human or veterinary subject that may involve a cell-signaling pathway. In addition, the cell can be from any multicellular organism, such as a plant, animal, fungi, or a single cellular organism. The cell can remain part of the multicellular organism or be separated from the multicellular organism.

Aspects of this disclosure are drawn to any process, product, method, system and composition of matter as disclosed herein, for example as shown and/or described in the specification and drawings.

EXAMPLE

Controlling ERK Activation Dynamics in Mammary Epithelial Cells with Alternating Electric Fields Through Microelectrodes Materials and Methods MCF10A cells co-express ERKAR3 and ERKTR-mCherry (Reference 17) were cultured in customized chamber with microelectrode arrays fabricated on the bottom cover slip for EF stimulation during imaging. The cells were starved for 2 his in EGF-free medium before experiments. AC EF was generated by a NI 9269 module from National Instruments as the cells were imaged on an inverted microscope with an incubator chamber, Data processing and statistics were performed using Matlab (MathWorks) and Igor Pro (WaveMetrics).

Chemical and Reagents

EGF (Cat #PHG1311), DMEM/F-12 (Cat #11320033), DMEM/F-12 no phenol red (Cat #21041025), Horse Serum (Cat #26050088), BAPTA AM (Cat #B1205) and Cell Viability Imaging Kit (Cat #R37609) were obtained from Life Technologies, Insulin (Cat #19278), Cholera Toxin (Cat #C8052), Hydrocortisone (Cat 410888), Trolox (Cat #D2650) and sulfuric acid (Cat #258105) were obtained from Sigma-Aldrich. Gefitinib (Cat #S1025), Trametinib (Cat #52673), Afatinib (Cat #S1011) Erlotinib and Gefitinib were from Selleck Biochemicals. Sorafenib (Cat #50-155-710) was from BIOTANG Inc. Cetuxitnab (NDC 66733-958-23) was from ERBITLIX. FNC (Cat #NC9971265) coating was from ATHENA ES. 30% hydrogen peroxide (Cat #3984) was from GFS Chemicals. PMMA (Cat #950PMMA A4) was from MicroChem. Silicone elastomers (Cat #KWIK-SIL) was from WPI.

Cell Culture

MCF10A co-express ERKAR3 and ERKTR was described in reference (17). Briefly, MCF10-A cells stably expressing EKAR3 were generated by cotransfection of pPBJ-EKAR3-nes and pCMV-hyPBase transposase vector. Then the MCF10A cells stably expressing EKAR3 were infected by retroviral particles of ERKTR constructed by co-transfecting 293T cells with pMSCV-puro-ERKTR-mCherry and pCL-Ampho.

The MCF10A cells were cultured in Dulbecco's modified Eagle's medium (DMEM)/F-12, supplemented with 5'%© horse serum, EGF (20 ng/ml), insulin (10 mg/ml), hydrocortisone (0.5 mg/ml), cholera toxin (100 ng/ml), penicillin (50 U/ml)), and streptomycin (50 mg/ml).

Fabrication of Chips and Assembly of Chamber

Before microelectrode fabrication, the commercial microscope cover glass (Thermo Scientific. Lot No: 17931) is treated with Piranha solution, a 3:1 volume mixture of concentrated sulfuric acid (Sigma-Aldrich. Product No: 258105-500ML) with 30% hydrogen peroxide (GFS Chemicals. Item No: 3984), heated at 80° C. for 30 minutes in order to clean organic compounds off and hydroxylate the glass surface. A 740 nm thick silicon oxide layer is then deposited on the glass surface via plasma enhanced chemical vapor deposition (PECVD) system (Oxford PLASMALAB 100 PECVD) to increase the surface uniformity and smoothness. Microelectrode array structure fabrication includes three main steps. First, a microelectrode array (bilayer structure of Cr/Au 1.5 nm/25 nm) in the center area of the chip, which is defined by OAI Model 808 MBA Mask Aligner, is deposited via Cressington 308R Thermal Evaporator system. Second, an outer electrode for connections (bilayer structure of Cr/Au 1.5 nm/50 nm), which is defined by GCA 8500 Stepper, is deposited via Cressington 308R Thermal Evaporator system. Third, a uniform Hafnium oxide coating is deposited via atomic layer deposition (ALD) system (Cambridge NanoTech Savannah ALD system) on top of the chip for passivation excepting the connection pads. Printed circuit board (PCB) interface is designed as an interface of connecting the microelectrode array to AC function generator are outsource fabricated by Sunstone Circuits. The cell chamber is designed as a medium reservoir and channel confinement and fabricated with polycarbonate plate (McMaster Carr. Catalog No: 8574K281) with a milling machine. Before the experiment, the chip is fixed on the PCB surface using PMMA (MicroChem. 950PMMA A4) and connected to the PCB via a wire-bonding machine (7476E Wedge-Wedge Wire Bonder, West-Bond, Inc.). The cell chamber is fixed and sealed on the surface of the chip with silicone elastomers (WPI. Catalog No: KWIK-SIL).

Live Cell Imaging

A special cell culture chamber was built to enable long term culture as well as observation and stimuli delivery. The culture well was made by assembling glass cover slips inside polycarbonate blocks cut by CNC. Cross-section view of the structure was shown in FIG. 1D. The confined channel of 170 μM height would allow good transparency, low background from the culture media, as well as provide a confined geometry and unify the electric field.

Time-lapsed imaging was conducted using a Zeiss Axio observer Z1 microscope equipped with an automated stage, filter turret, as well as an environmental chamber. Images were obtained through a 10× EC Plan-Neofluar Ph1 objective with 0.3 numerical aperture and recorded with a QImaging Retiga R6 Large Field of View Scientific CCD camera using MetaMorph software. The following filter sets were used: YFP, 46 HE; RFP, 43HE.

Cells were prepared for imaging in chambers with FNC, and subsequently seeded with MCF10A-ERKTR-EKAR3 cells. In order to minimize background fluorescence during live cell imaging, the complete growth media was replaced 2 h prior to cell imaging by a low fluorescence medium consisting of DMEM/F12 lacking phenol red, and supplemented with hydrocortisone (0.5 mg/ml), cholera toxin (100 ng/ml), penicillin (50 U/ml), and streptomycin (50 mg/ml). Prepared chambers were imaged on the Zeiss Axio observer Z1 microscope with an incubator to maintain the culture at 37° C. in 5% CO2 throughout the course of the experiment.

AC Stimuli Application

The 50 k Hz bipolar square wave AC stimuli were designed in LabVIEW and were delivered by the compactRIO controller (NI cRIO 9030 platform, National Instruments) and NI 9269 4-channel Voltage Output Module (National Instruments) controlled by customized LabVIEW software. Connection from the cRIO controller to the chip was made through a custom built PCB with gold coating. Connection between PCB and the microelectrodes were made by wire bonding machine (7476E Wedge-Wedge Wire Bonder, West-Bond, Inc.)

Electrochemical Test

The cyclic voltammetry scan was performed using Keithley 2636B source meter and Igor Pro (Wave Metrics) as software interface. The scan was carried out in 5 mM ferrocyanide/ferricyanide solution with 0.1 M KCl as support electrolyte. For three electrodes setup, Ag/AgCl was used as reference electrode and platinum wire as counter electrode; for two electrodes setup, one electrode was used as working electrode and the other electrode used as ground to mimic the application of EF stimuli.

Simulation of Electric Field Distribution Between Two Electrodes

The electric field simulation was performed in COMSOL. Multiphysics 5.3 using the finite elements method. To simplify the simulation of the microelectrode array, one electrode pair was modelled as two gold electrodes with 200 µm gap in between on a 10 µm thick, 1200 µm×1200 µm silicon dioxide substrate. The length, width and the height of the electrode are 100 µm, 10 µm, 50 nm respectively, and the whole electrode pair was set in aqueous solution (dielectric constant=78).

EGF, Inhibitor and Antibody Tests

The inhibition of ERK activation were performed using AC EF in the custom EF chamber and using EGF in 96-well plate respectively. 2 hours prior to imaging, the growth medium was replaced with the customized aforementioned low fluorescence medium (DMEM/F12 lacking phenol red) with hydrocortisone, cholera toxin, penicillin and streptomycin), supplemented with the indicated concentrations of EGF, antibody or the inhibitor and then observe cell reaction responding to EF and EGF respectively under microscope.

Membrane Integrity Test

To test cell membrane integrity, after cell plating in the channel, 50 µM Sytox orange (Invitrogen) were added in the medium, 1.5V AC EF stimulation was continuously applied for >30 minutes while monitored by microscope. Fluorescence image were taken with excitation filter of 525-535 nm and emission filter of 550-600 nm.

Cell Viability And Proliferation Rate Tests

Cell viability test were performed using the Cell Viability Imaging Kit (Cat #R37609, Life Technologies). Two drops of the reagent were added to the medium in the chamber 15 minutes prior to the imaging. NucBlue® Live reagent (Hoechst 33342) stains the nuclei of all cells imaged by DAPI filter set; and NucGreen® Dead stains the nuclei of dead cells with compromised plasma membranes, imaged by GFP filter set. Cell proliferation was evaluated by cell counting. AC stimulation regions are within 150 µm from the electrodes. Control regions were selected more than 200 µm away from the electrode where no ERK activities were observed. We first counted the cells before AC EF stimulation on day one. The cells are then put back in the incubator for 24 hours. On day two we then confirmed that AC EF could activate the cells in the same region and counted the cells again. The two counting numbers were used to calculate the proliferation ratio, Four sets of ratios from two independent experiments were used to compare AC EF stimulation with control group.

Evaluation of the Spontaneous ERK Activity at Different Temperatures

The temperature is regulated by the on-stage incubator, and changed in 1° C. steps from 37° C. to 39° C. and then continuously cooling back to 35° C. again. For each temperature, the cell is allowed to settle for >10 minutes, and the ERK activity level is evaluated by fluorescence imaging of the ERKTR reporter.

Evaluation of Local Temperature Changes by Patch Clamp Measurements

Patch clamp pipettes were prepared from Borosilicate capillary glass (GC150-10, Warner Instruments, O.D. 1.5 mm, 0.86 mm) with a micropipette puller (P-1000, Sutter Instruments). The pipette was filled with 0.1 M KCl and mounted on a patch clamp amplifier (EPC800 USB, HEKA) using Ag/AgCl as the reference electrode. 10 mV of bias is applied to the pipette and the current output is recorded using an ITC-18 data acquisition system from HEKA with sampling rate of 20 kHz. With room temperature regulated at 21.6±0.2° C., the pipette tip is positioned in a clean chamber with cell culture medium in the middle between a microelectrode pair and 10 µm above the surface of the substrate with a micromanipulator (MP-225, Sutter Instrument). Another Ag/AgCl reference electrode is sealed in 0.1M KCl and connected to the chamber through a salt gel bridge. If temperature rise, the ion mobility would increase and result in higher conductivity. Since the tip of patch clamp has a diameter of only ~1 µm, the conductivity of the pipette electrode would be highly sensitive to local temperature change at the opening. (21) Ten recordings for each set of configurations of microelectrode types and stimulation time were taken, in which the first 10 minutes was recorded without AC EF stimulation as the silence period. The silence period is used to correct any slow drifting of current during the recording, which happened in both increasing or decreasing directions, but consistently within one preparation of recording. The overall linear drift of current level during the whole recording (3 hrs) typically within 5%-15%, and for each experiment (20 min) the linear drift is typically within 2%. After the drift correction, the 60 sec of data immediately before the start and after the end of the AC EF stimulation were used to calculate the change of the local temperature based on the model and analysis of (21). Specifically, temperature is calculated from Arrhenius equation:

$$T = \frac{1}{\frac{1}{T_0} - \frac{R}{E_a}\ln\left(\frac{I}{I_0}\right)}$$

Where R is the gas constant, T0 is the starting room temperature (21.6° C., 294.75 K), I is the pipette current at T, and I0 is the pipette current at T0. Ea is the nominal activation energy, which is estimated to be 16.07 kJ/mol (21).

Data Processing

Data processing and statistics were performed using Matlab (MathWorks). The method for cell identification and tracking were described in previous paper, using the YFP channel fluorescence of EKAR3 which is confined to the cytosol by a nuclear localization sequence (1). After segmentation, high intensity regions in the YFP channel were marked as nuclei, and the neighboring 7 pixel outside the nucleus were recognized as region of cytosol. Cell ERKTR ratio was calculated by the ratio of average RFP fluorescence intensity in cytosol vs nucleus of each cell. ERK activation was determined by the first time point when ERKTR ratio rose above 6 standard deviations of the resting state. Cell recovery time were determined by the peak-finding function of Matlab.

Estimation of Impedance of the Microelectrodes

Without HfO2 Coating

The electrical double layer (EDL) has a capacitive impedance, which can be calculated based on the classical Gouy-Chapman theory.
The ionic strength of the culture media, I, is:

$$I = \frac{1}{2}\sum_{i=1} Z_i^2 n_i = 0.19\text{M}$$

Where $Z_i$ and $n_i$ are the charge and the mole concentration of the ion species respectively. The Debye length is:

$$d = \left(\frac{\varepsilon kT}{2Ie^2 N_A}\right)^{\frac{1}{2}} = \frac{0.304}{\sqrt{0.19}} = 0.697 \text{ nm}$$

Where k is Boltzman's constant, T is the absolute temperature, e is the proton charge, $\varepsilon$ is the permittivity of the solvent and $N_A$ is Avogadro number.
Thus the capacitance of the EDL is:

$$C_{EDL} = \frac{\varepsilon A}{d} = 2.7 \times 10^{-8} F$$

Where A is the area of the electrode and $\varepsilon$ is the permittivity of the solvent.
The impedance of EDL on the electrode surface at 50 kHz is:

$$Z_{EDL} = \frac{1}{j\omega C_{EDL}} = \frac{1}{j}117.9\Omega$$

According to the calculation above, the impedance between two bare Au electrodes is:

$$Z_{noHfO2} = R_{sol} + 2 \times Z_{EDL} = 5.2 + \frac{1}{j}0.118 k\Omega$$

With HfO2 Coating

The ALD $HfO_2$ has a dielectric constant around 18, and then the capacitance of a 10 nm thick ALD $HfO_2$ layer is:

$$C_{HfO2} = \frac{\varepsilon_r \varepsilon_0 A}{t} = \frac{18 \times 8.854 \times 10^{-12} \frac{F}{m} \times 0.0275 \text{ mm}^2}{10 \text{ nm}} = 0.4384 \times 10^{-9} F$$

Where A is the area of the electrode, $\varepsilon_r$ is the relative permittivity of ALD $HfO_2$, $\varepsilon_0$ is the permittivity of vacuum and t is the thickness of the ALD $HfO_2$ layer
Thus the impedance of the 1.0 nm thick ALD $HfO_2$ at 50 kHz is:

$$Z_{HfO2} = \frac{1}{j\omega C_{HfO2}} = \frac{1}{j}7260\Omega = \frac{1}{j}7.3k\Omega$$

Where $\omega = 2\pi f$, f is the AC signal frequency.
So the impedance between two 10 nm HfO2 coated Au electrodes is:

$$Z_{withHfO2} = R_{sol} + 2 \times Z_{EDL} + 2 \times Z_{HfO2} = 5.2 + \frac{1}{j}(0.24 + 14.6)k\Omega$$

Resistance of Solution Between the Electrodes

Figure 22:
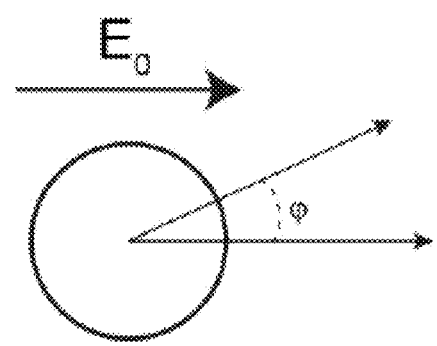
FIG. 22. An estimation of cross-membrane potential at difference AC EF frequencies.

Based on the recipe of the culture media DMEM/F-12(Cat #21041025, Life Technologies), the medium conductivity is:

$$\kappa = \sum \Lambda_i \cdot c_i = 13.92 \times \frac{10^{-1} S}{m} = 1.392 \frac{S}{m}$$

Where $\Lambda_I$ is the molar conductivity of ion i in the medium, and $c_I$ is the concentration of ion i. Thus a simple estimation of the medium resistance between two electrodes is:

$$R_{sol} = \frac{d}{\kappa A} = \frac{200 \text{ um}}{\frac{1.392 S}{m} \times 0.0275 \text{ mm}^2} = 5.2 \text{ } k\Omega$$

Where d is the distance between two electrodes.
This impedance analysis shows that the capacitive impedance of the $HfO_2$ layer at 50 kHz is comparable to the resistance of the medium layer between the electrodes.
An estimation of cross-membrane potential at different AC EF frequencies is shown in FIG. 22.

We assume that: (1) The cell is round, and the thickness of the membrane is far less than the cell radius; (2) The resistivity of the membrane is infinite; (3) The conductivity of the solution outside the cell is uniform.

If the frequency is below 100 kHz, the potential cross the cell membrane can be approximated by:

$$\psi(j\omega) = \frac{3}{2} E_0 R \cos\varphi \frac{1}{1 + j\omega\tau_m}$$

$$\text{where } \tau_{m1} = RC_m\left(\frac{1}{\sigma_1} + \frac{1}{2\sigma_e}\right)$$

If frequency is higher than 100 kHz, we can use the following formula:

$$\psi(j\omega) = \frac{3}{2} E_0 R \cos\varphi \frac{1 + j\omega\tau_{m2}}{1 + j\omega\tau_{m1}}$$

$$\text{where } \tau_{m1} = \frac{\varepsilon_m}{\frac{d}{R} \frac{2\sigma_e \sigma_1}{\sigma_1 + 2\sigma_e} + \sigma_m}, \tau_{m2} = \frac{\varepsilon_1 + 2\varepsilon_e}{\sigma_1 + 2\sigma_e}$$

The meaning of the symbols: $\omega = 2\pi f$: the angular frequency of the EF applied; R: the radius of the cell; $\sigma_1$, $\sigma_e$: conductivity of the Cell cytoplasm, and solution outside the cell;

$$C_m = \frac{\varepsilon_m}{d}:$$

Capacitance per unit area of the cell membrane; $\varepsilon_m$: Cell membrane permittivity; d: membrane thickness; φ: the angle between the imposing electric field and the position of the observation.

Results

The ERK signaling pathway regulates critical cell behaviors, including, for example cell motility, survival, proliferation and fate determination/differentiation[1-9]. Aberrant signaling of this pathway underlies many important diseases, including cancer and diabetes[10,11]. How are such diverse consequences coded by ERK activation? Recent advances in imaging the dynamics of ERK activation with single cell resolution have started to reveal critical coding mechanisms and rich information embedded therein. For example, the decision to enter S phase and proliferation of mammary epithelial cells (MCF10A cells) is influenced by the frequency of ERK activation[1]. The change in ERK dynamics in PC12 cells modulated by different pulsed EGF stimulations can decide whether they proliferate or differentiate into neuron-like cells[8,9]. In addition, the critical roles of ERK activation dynamics in vivo have also been demonstrated. In mouse epidermis, upon injury, ERK activation propagates as waves in parallel to the wound edge and is associated with G2/M cell cycle progression[12]. In C. elegans development, Ras-mediated cell fate specification involves different spatiotemporal pulses of ERK activation[13].

A practical method to control the frequency as well as amplitude of ERK activation will be of great value in both basic research as well as possible clinical applications. Frequency modulation (FM) of ERK activation has been achieved with optogenetics, where genetically modified light sensitive molecules are expressed in target cells and light signals are shined at controlled frequency upon cells[14]. Another method of FM is through pulsed stimulation with EGF (epidermal growth factor), in which addition and washout of EGF is repeated at required frequency[8,15].

We report here a method of frequency modulation of ERK activation that does not require repeated addition and washout of chemicals, or genetic-modification of cells. We used an alternating current (AC) electric field (EF) stimulation to induce defined FM of ERK activation, We show that time-modulated symmetric bipolar AC EF of tens of kHz can directly trigger highly localized and synchronized ERK activation without Faradaic process. We provide evidence for selective AC EF induced ligand-independent EGFR phosphorylation. Our work suggests a new strategy and practical technology of precise ERK modulation with high spatial resolution and temporal control, and may have significant implications for design of electroceuticals to regulate important biological processes and treat diverse diseases through FM of intracellular signaling pathways.

Firstly, we briefly introduce the ERK activation reporter used in our experiment and the design of the microelectrode chip. ERK translocation reporter (ERKTR) can be used to report activation dynamics of ERK in a spontaneously immortalized mammary epithelial cell line (MCF10A)[16,17]. Upon activation of EGFR-Ras-ERK pathway, the mCherry-labelled ERKTR is phosphorylated and translocated from the nucleus to the cytosol, causing fluorescence intensity decrease in the nucleus region and increase in the cytosol (FIG. 1A). The ratio of fluorescence intensity in the cytosol (Fc) and that in the nucleus (Fn), i.e., ERKTR ratio, thus gives a quantitative in situ assessment of ERK activation of an individual cell with high temporal resolution (see Materials and Methods). With this real-time reporting system, the following two questions were addressed: (1) How precisely in space and in time can we control ERK activation with EF? (2) What is the possible mechanism that EF couples with the ERK signaling pathways?

Figure 6A:
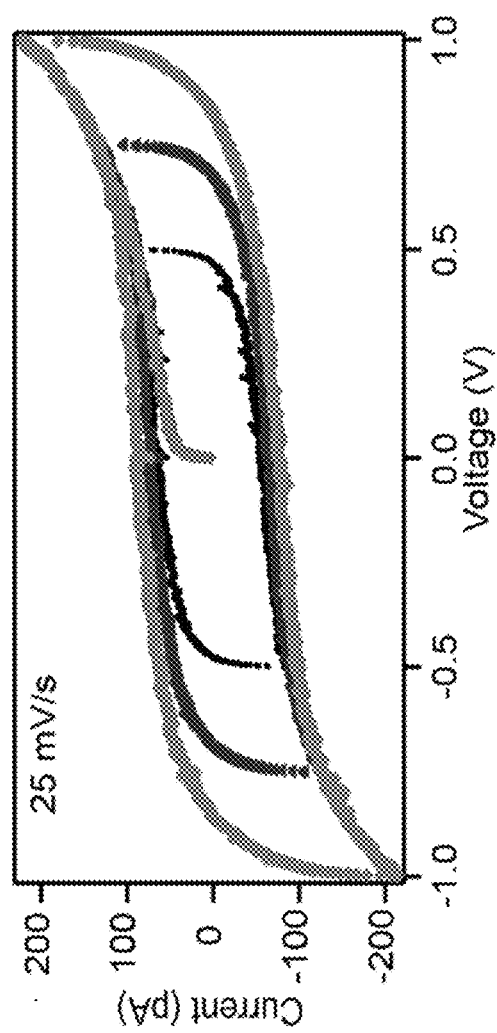
FIGS. 6A and 6B. Evaluation of electrode stability.
Figure 6B:
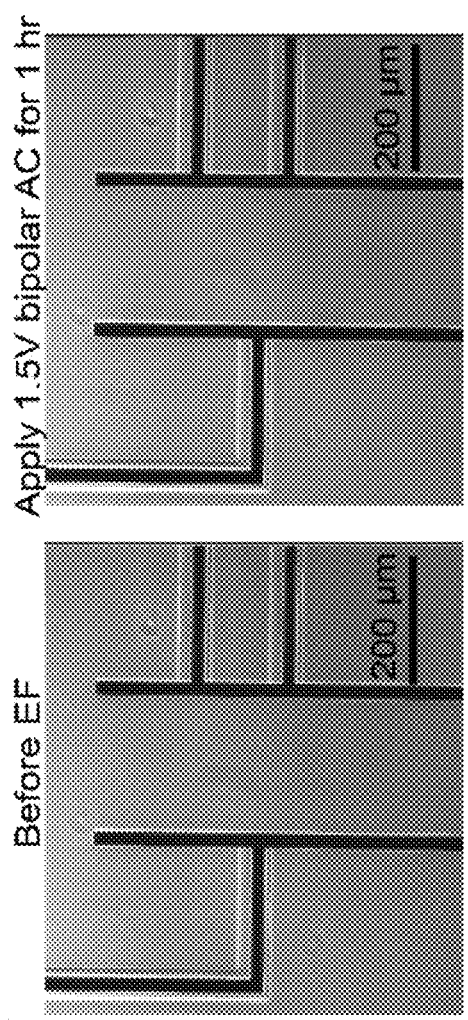
Figure 7A:
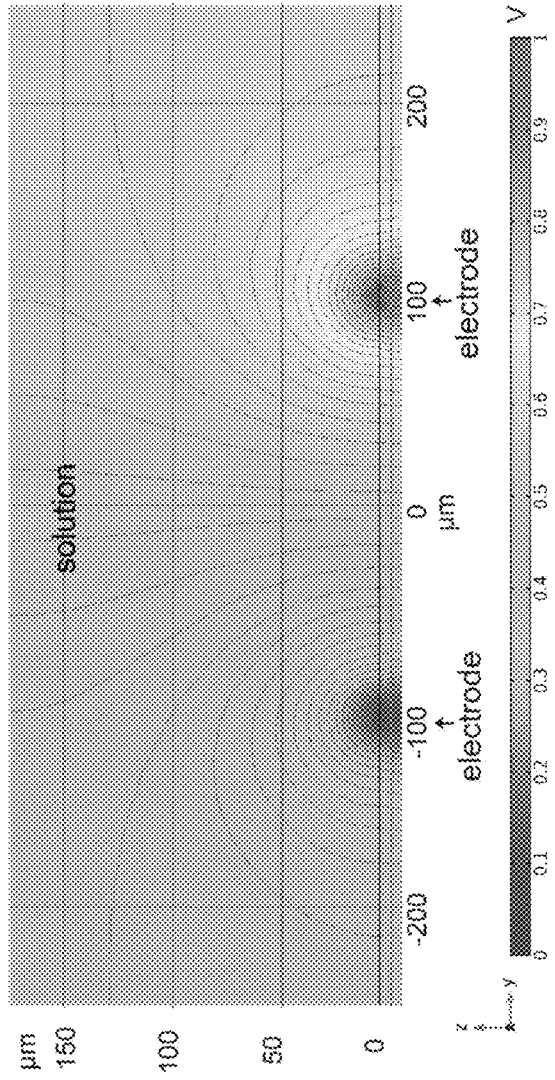
FIGS. 7A and 7B. Simulation of electric field distribution between two electrodes.
Figure 7B:
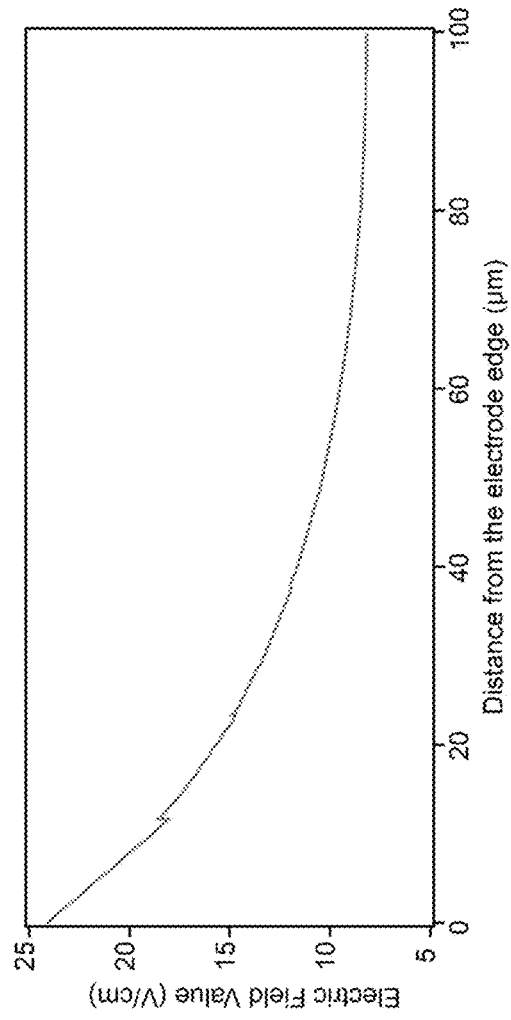

To address these questions, we prepared customized microelectrode chips to deliver local EF to the cells with several key considerations. First, a pair of microelectrodes were used to interface with the cells so that the EF was localized close to the electrodes and decayed rapidly outside the vicinity. The electrodes were fabricated by top-down lithography on a 170 μm thick glass cover slip. The metal connections were passivated by a layer of SU-8 epoxy by photolithography, leaving only the parallel electrode bars exposed, which had an edge-to-edge distance ranging between 50 to 200 μm (FIG. 1B). Second, bipolar symmetrical electric pulses were used in our experiments to eliminate net direct current (DC) ionic flows in the system. Specifically, due to the small exposed surface area of the electrodes, the electric signals were coupled to the medium capacitively as through a high-pass filter with an impedance of ~120Ω at 50 kHz. The designed signal has fast rising and falling edges and a width of 10 μs to enhance the potential drop within the medium (FIG. 1C). Third, the electrodes and circuits connected to them were isolated from all other grounds. We have performed cyclovoltammetry on these electrodes in the assay medium and there was no significant redox current in a slow voltage sweep between −1.0 V and 1.0 V (See FIG. 6A), In addition, the stability of the electrodes was tested with prolonged application of up to ±1.5 V bipolar pulses for >1 hour and no degradation of the metal surface was observed (See FIG. 6B). The simulation of the EF distribution (COMSOL Multiphysics, see Materials and Methods) showed that when an AC (1 V, 50 kHz) was applied between a pair of metal electrodes 200 μm apart in homogeneous medium, the EF strength close to the surface of the substrate and at the center of the electrode pair was ~8 V/cm, and close to the edge of the electrode ~24 V/cm (See FIG. 7). Last, the chip was assembled into an observation chamber with a thin fluidic channel over the electrode arrays (W 0.5 cm×L 1.0 cm×H 170 μm) where cells were plated and cultured. After wire bonding, the chamber can be mounted on an inverted microscope for imaging as EF stimuli were applied (FIG. 1D) (Materials and Methods).

Secondly, we studied the localized activation of ERK by AC EFs on our platform. About 3-6 minutes after onset of stimulation, fluorescence intensity of the nuclei started to decrease and fluorescence intensity of cytosol increase, indicating ERK activation. FIG. 2A is a typical image took at 9 min after the EF stimuli delivery. The majority of cells close to the electrodes demonstrated clear ERK activation (FIG. 2B). Cells more than 200 μm away from the electrode region remained silent, including those that were close to the SU-8 passivated connections (FIG. 2C).

Figure 8A:
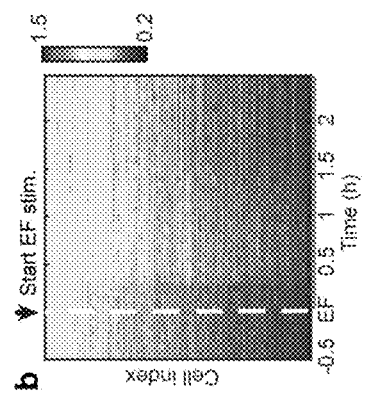
FIGS. 8A and 8B.
Figure 8B:
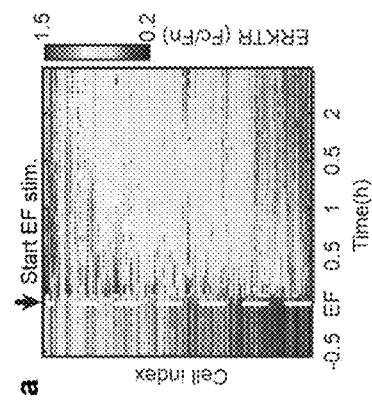

ERK activation indicated by the ERKTR ratio (Fc/Fn) demonstrated synchronized initial response with heterogeneous dynamics for cells resided within 100 μm from the electrodes. Before onset of EFs, only very few displaying limited low-level spontaneous ERK activity. About 9 minutes after onset of the stimulation, cells showed ERK activation with different amplitude and duration (FIG. 2D). Majority of the cells showed response between 6 min to 18 min following onset of the stimulation. Under continuous EF exposure, the ERK activation level of the majority of cell population gradually decreased towards the baseline in 29±13 minutes. Cells that are far away from the open electrode area showed no ERK activation by EF (FIG. 2E). The heat maps summarizing the ERK activation in both areas are given in FIGS. 8A and 8B.

Figure 3B:
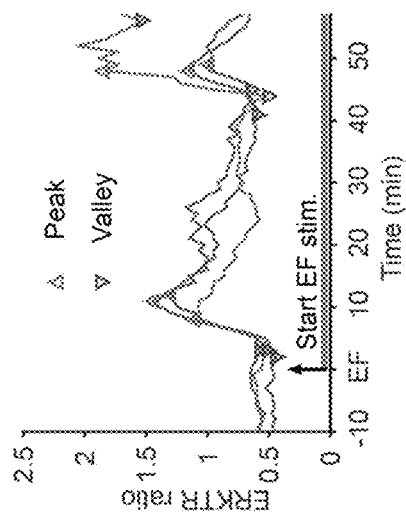
Figure 3C:
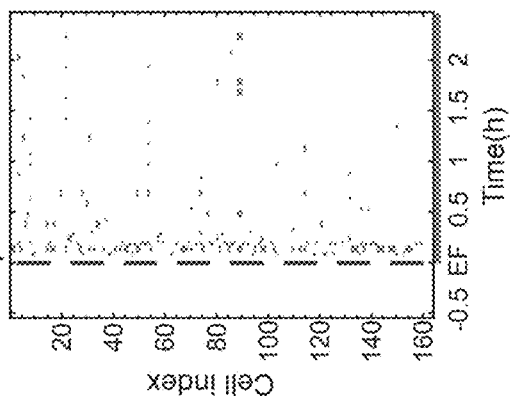
Figure 9:
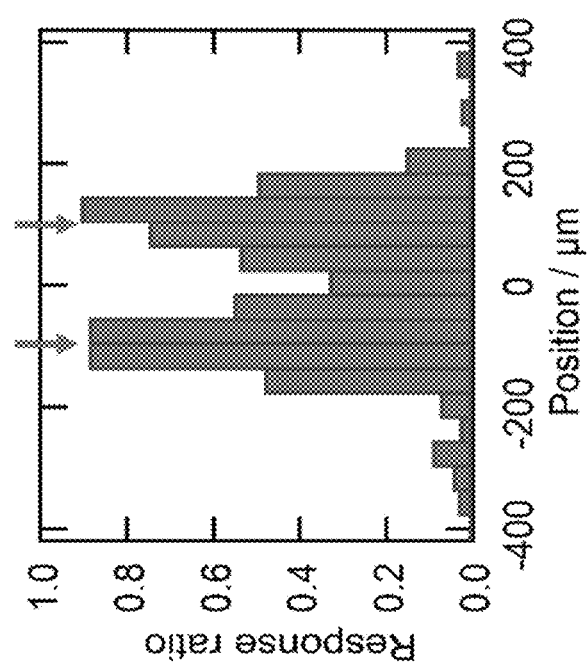
FIG. 9. Population ratio of cells that showed ERK activation at different x-positions. The microelectrodes are placed perpendicularly to the x-axis. The red arrows mark the x-position of the pair of microelectrodes FIGS. 10A and 10B. Cell membrane impermeable fluorescence dye Sytox orange (50 µM) staining result.

We note that activation of ERK is highly localized: more than 80% of cells within the range of 50 μm from the electrodes showed clear ERK activation, and the ratio decreased rapidly to below 20% as the distance increased to more than 100 μm. Very few cells showed ERK activities 300 μm away from microelectrodes (See FIG. 9). In addition, under extended EF stimulation, oscillatory patterns in the ERK level could be observed for a small portion of the cells (FIG. 3A, 3B). The peaks and valleys of all the ERKTR ratio time traces were identified using a threshold method automatically (see Materials and Methods). About 20% of cells showed ERK activation cycle twice or more (FIG. 3C).

Figure 10A:
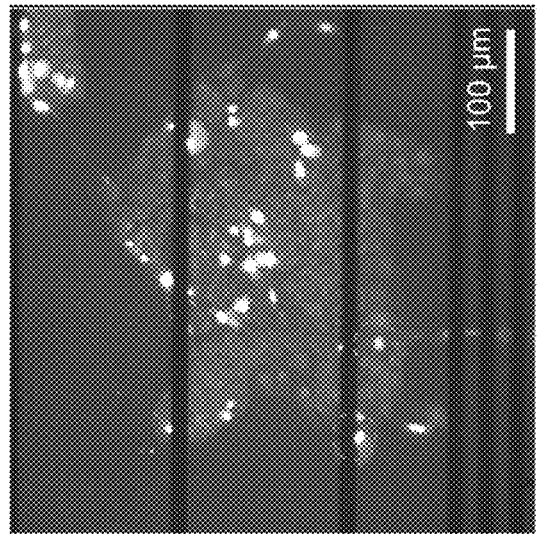
(FIG. 10A) Before EF stimuli was applied.
Figure 10B:
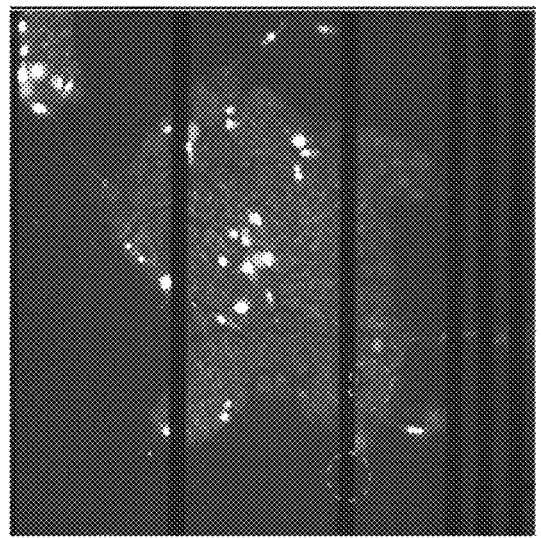
(FIG. 10B) after 1 hour of 1.5 V 50 kHz AC stimuli. Bright dots indicate cells with broken membrane. Only a couple of cells showed such change during this experiment (in the circle).

Thirdly, we show that no Faradaic process or electroporation were involved in the AC EF activation of ERK, and neither Ca2+ nor reactive oxygen species (ROS) mediated this process. To exclude the possibility of IRK activation related to cell damage[18], we investigated the possibility of cell membrane damage using membrane impermeable dyes. Sytox orange (50 μM, Invitrogen) which stains the nucleus and cannot penetrate intact cell membrane, was added in the medium, and AC EF stimulation was continuously applied for >1 hour. Except for very few cells that were in direct contact with the metal electrodes, almost all the cells remained unstained, suggesting no membrane damage (See FIG. 10A, 10B). In addition, cells were stained using the Cell Viability Imaging Kit (Cat #R37609, Life Technologies, see Materials and Methods), 2 hours after confirming the reproducible ERK activation. More than 95% of the cells remained alive and healthy after the experiment. We also calculated the proliferation rate of cells 24 hours after confirming EF activation of ERK as 1.26±0.11, which has no significant difference to the ratio 1.22±0.14 obtained from control groups (See Materials and Methods, FIG. 11.)

Figures 13A, 13B:
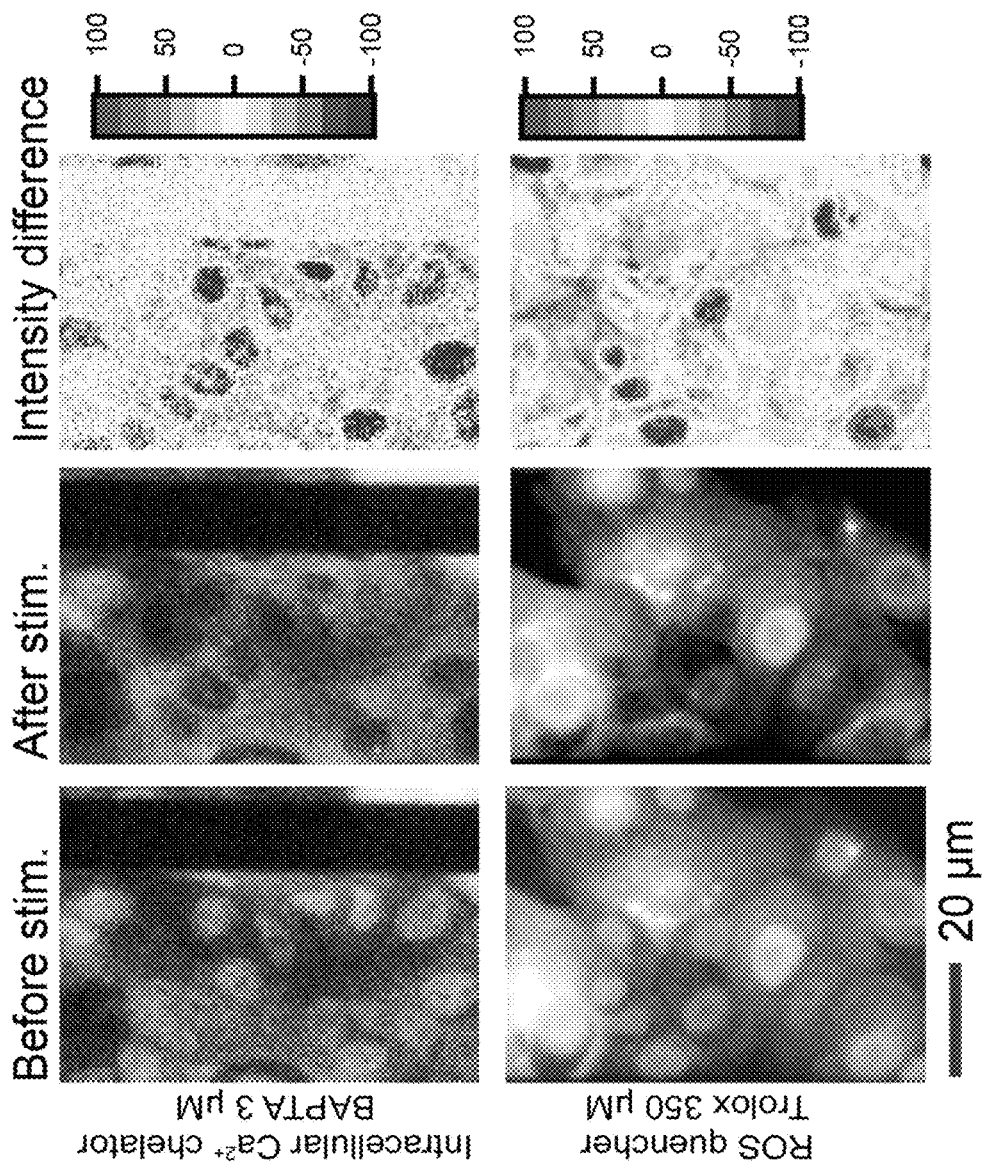
FIGS. 13A and 13B. ERK activation is independent of $Ca^{2+}$ and ROS. Cell response to EF stimuli, tested with intracellular Calcium chelator BAPTA AM (FIG. 13A) and ROS quencher Trolox (FIG. 13B).

To exclude any electrochemical reactions that could interfere with the EF activation of ERK, we added an extra layer of high-k passivation layer over the terminal electrode surface, which blocks all redox reactions while not increasing the impedance of the electrodes significantly (See FIG. 12A, 12B). Specifically, we deposited over the entire surface of the chip 10 nm HfO2 by atomic layer deposition (ALD). Cyclic voltamtnetry test (see Materials and Methods) confirmed that the HfO2 coating completely suppress the Faradaic process (see FIG. 12C). Our impedance analysis shows that the capacitive impedance of the added HfO2 layer at 50 kHz is about 7 kΩ, which is comparable to the resistance of the medium layer between the electrodes. With this new design of passivated electrodes, we showed that ERK can still be reliably activated by EF stimuli (see FIG. 12D), with an expected higher threshold pulse amplitude (typically between 1.5V~3V) due to the increase of the impedance. In addition, we have confirmed that neither Ca2+ chelator (BAPTA AM, 3 μM, Life Technologies), nor ROS quencher (Trolox, 350 μM, Sigma-Aldrich) could block the EF activation of ERK (See FIGS. 13A and 13B), which also suggests that ERK activation in our system is unlikely mediated by Ca2+ changes or ROS, contrary to previously suggested mechanism when DC EF stimulations were applied[19,20]. The observed activation of the ERK thus was not associated with redox processes at the electrode interface.

Figure 14:
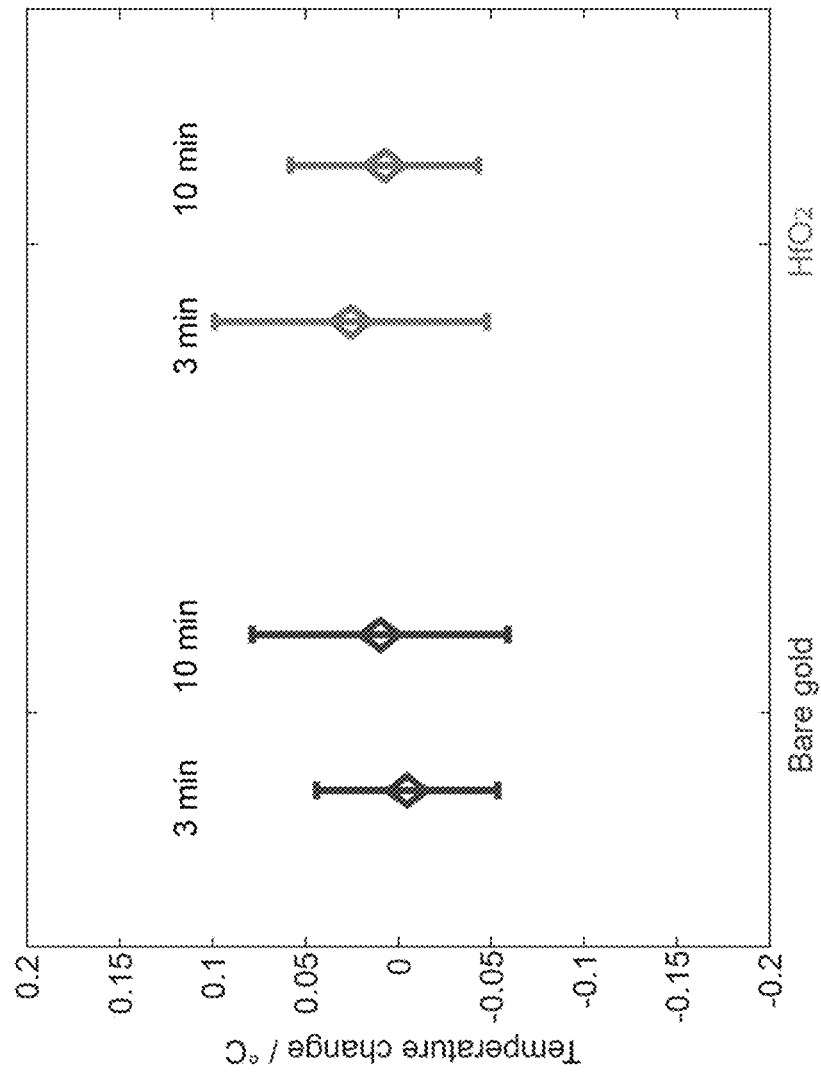
FIG. 14. Evaluation of local temperature change by monitoring the current changes of a patch clamp pipette electrode. Temperature change was measured with room temperature at 21.6±0.2° C., after applying AC EF stimulation for 3 and 10 minutes through bare gold electrodes (1V, 50 KHz square wave), and through HfO2 coated electrodes (6V 50 KHz square wave). The patch clamp pipette is positioned in the middle between the electrode pair and 10 µm above the surface of the substrate.
Figure 15A:
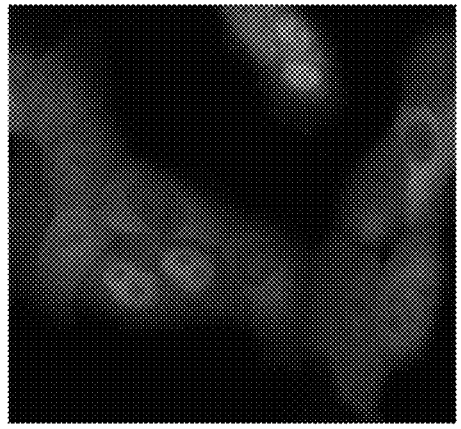
FIGS. 15A-15D. Cell response to temperature change.
Figure 15B:
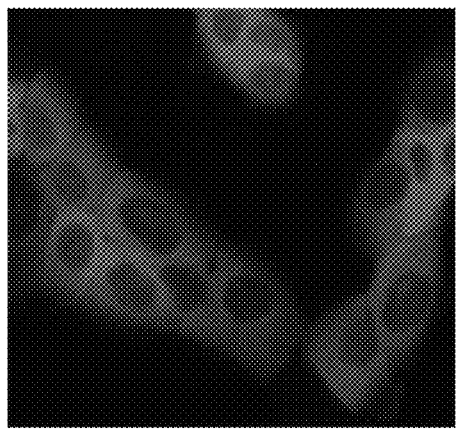
Figure 15C:
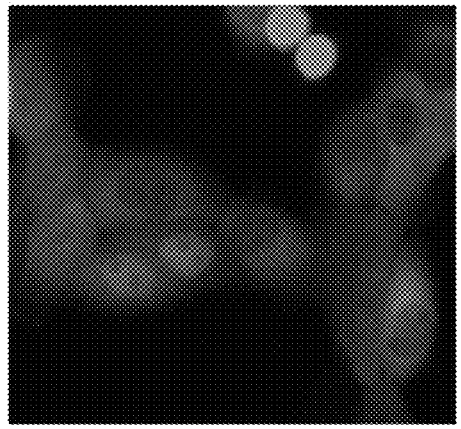
Figure 15D:
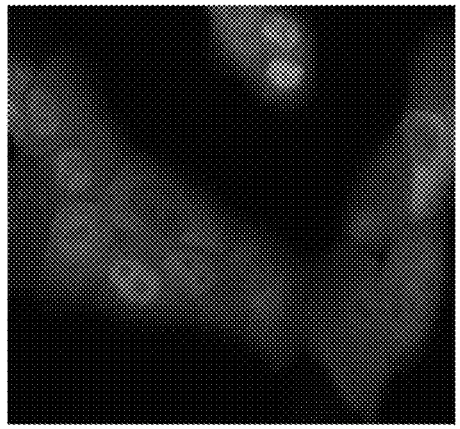

Fourthly, we demonstrate that no local temperature increase or diffusion limited process were involved in the activation or ERK. We measured the local temperature by tracking the current of a patch clamp pipette electrode before and after the application of AC EF[21]. A patch clamp pipette freshly prepared by a micropipette puller (P-1000, Sutter Instruments, see Materials and Methods) was filled with 0.1 M KCl, giving a typical resistance of 7-10 MΩ. The tip of the patch clamp pipette was positioned within 10 μm above the substrate between the electrodes in a clean chamber by a micromanipulator (MP-225, Sutter Instruments), using Ag/AgCl sealed in 0.1 M KCl as the reference electrode through a salt gel bridge. The room temperature was regulated at 21.6±0.2° C. A bias of 10 mV was applied to the pipette electrode as the current was monitored through a patch clamp amplifier (HEKA EPC 800 USB). Since the current will be sensitive to the local temperature at the very opening of the pipette, we can use the current to evaluate the local temperature changes. Ten groups of measurements were performed for 3 and 10 minutes of AC EF stimulations each. When bare Au microelectrodes were used, the calculated temperature change was 0.00±0.05° C. and 0.01±0.07° C. respectively, and 0.03±0.07° C. and 0.01±0.05° C. respectively when HfO2 coated microelectrodes were used (See FIG. 14). Therefore, we conclude that there was no appreciable local temperature increase due to the application of AC EF stimulations in our setup in the course of the ERK activation. In addition, we exposed the MCF10A cells to different temperatures between 35° C. and 39° C., and the spontaneous ERK activities were most active between 35° C. to 37° C. Cells demonstrated much reduced spontaneous ERK activities at higher temperature (See FIG. 15). These data suggest that local temperature increase was not involved in the observed ERK activation.

In addition, we have studied the onset time of the ERK response for cells at different distances (0-100 μm) from the electrodes. Cells have overall shown clear timing variations in their responses such that the onset time of the ERK activation scattered in a wide range from 6 minutes up to 36 minutes (See FIGS. 16A-16C). Interestingly, more than 79% cells (n=216) were activated within 15 minutes independent of where they were, which strongly suggested a direct interaction with the AC EF. On the other hand, <21% of the cells, all of which were >25 μm away from the electrodes, showed 18-36 minutes onset time that appeared rather randomly distributed, which could be attributed either to spontaneous activities, or a diffusion-related process, for example, intercellular communications. In addition, if Joule heating related process were involved, since the current density was higher where it was closer to the electrodes, more pronounced temperature changes would happen faster near the electrodes and slower at farther distance, which was not observed from the onset time distribution. Therefore, this result also suggested that temperature change was not an important factor.

Figures 17A, 17B:
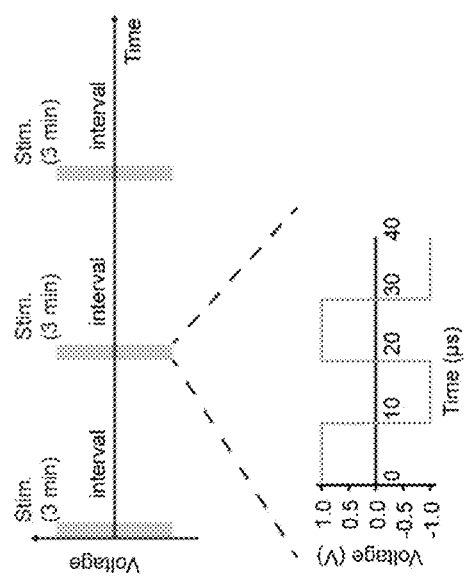
FIGS. 17A and 17B. Waveform of the intermittent AC EF stimulation used in FIG. 4 (FIG. 17A) Overall 3 minutes of AC EF stimuli were delivered with 50 minutes interval silent time.
Figure 18:
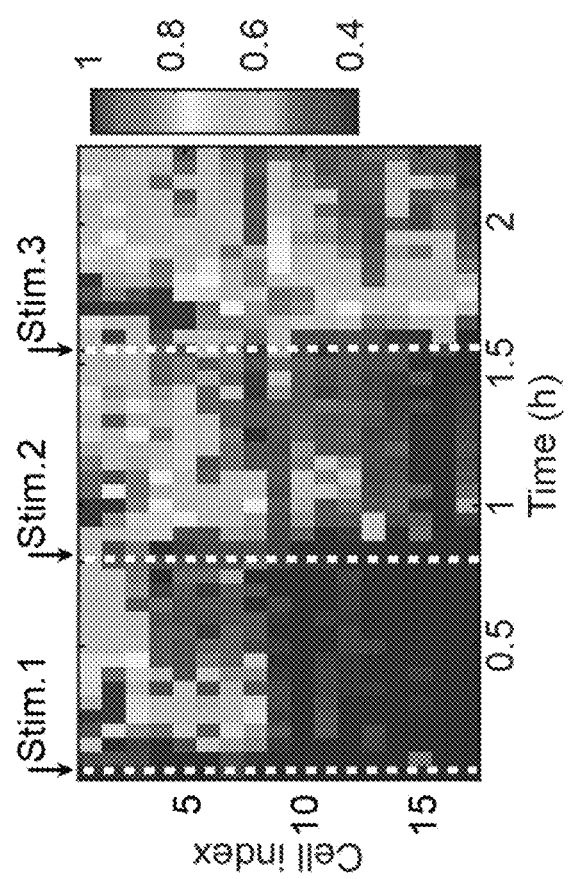
FIG. 18. Heat map plot showing synchronized ERK activation by repeated short AC-EF stimulation in FIG. 4. Warmer color indicates higher ERKTR ratio and higher level of ERK activity.
Figure 19B:
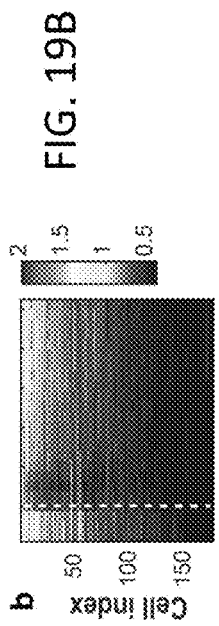
FIGS. 19A-19G. Heat maps summarizing the time evolution of ERKTR ratio for blocker tests in FIG. 5 of the control group (FIG. 19A), and of cells with MEK inhibitor Trametinib (FIG. 19B), Raf inhibitor Sorafenib (FIG. 19C), tyrosine kinase inhibitor (TKI) afatinib (FIG. 19D), TKI Erlotinib (FIG. 19E), TKI Gefitinib (FIG. 19F), and EGFR binding-site antibody (FIG. 19G), respectively.
Figure 19D:
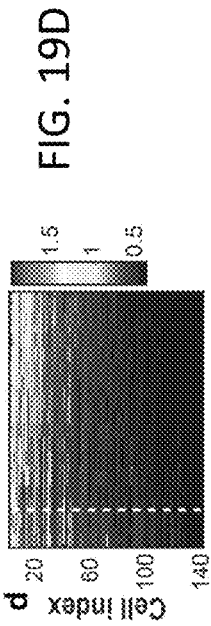
Figure 19F:
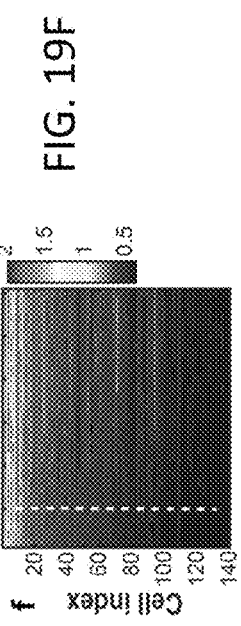
Figure 19A:
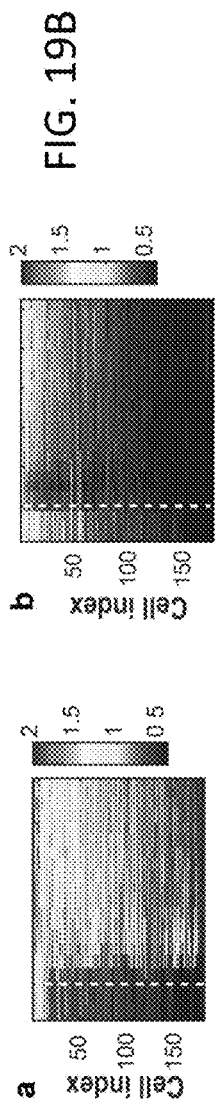
Figure 19C:
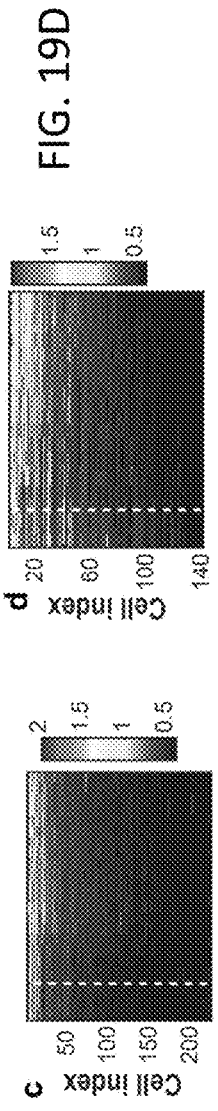
Figure 19E:
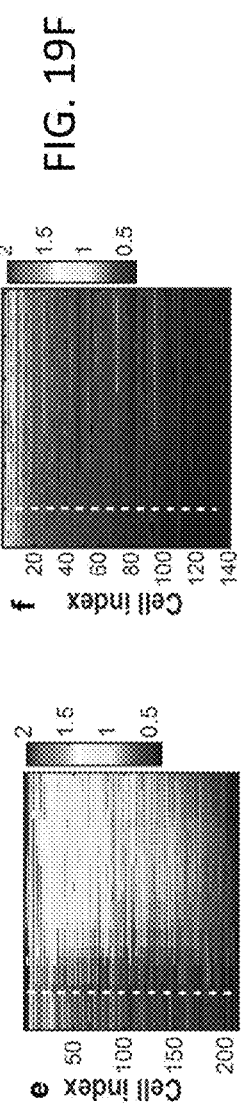
Figure 19G:
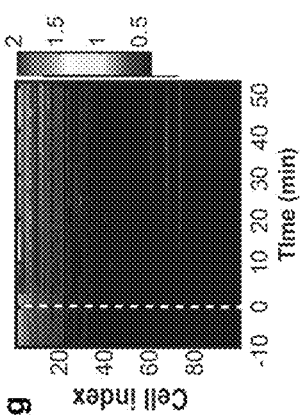

Fifthly, we demonstrate that the ERK activation can be precisely synchronized and modulated by AC EFs. Given the localization and synchronized onset of the ERK activation by AC EF, it is therefore possible to control the frequency of the ERK activation for a selected population of cells simply by cycling AC EF on and off with the right timing. As an example, we have achieved very robustly synchronized and enhanced ERK activation at a rate of about twice per hour. Specifically, in one cycle, a 3 min train of bipolar pulses was delivered to the electrodes, during which time no cell response generally has started to appear yet, followed by a ~40 min period in which the EF is turned off. This cycle was repeated for three times in the experiment (See FIGS. 17A and 17B). Three activation events are readily observed 3-6 minutes following the AC EF stimuli at 0 minute, 48 minute, and again 93 minute as shown in FIG. 4A. The time traces of the ERKTR ratio showed three distinct activation peaks (FIG. 4B), which are also evident in the heat map plot (See FIG. 18) and peak time map (FIG. 4C). We noticed that if the duration of EF stimulation in each cycle is reduced shorter than 3 min, we observed less reproducible ERK activation in much fewer cells. In addition, since the time interval of our image sequence is currently limited to 3 minutes, the selected snapshots might not capture the maximum response of all cells.

From FIGS. 4A-4C, we can see that 50% of the cells within 100 μm range from the electrodes showed repeated ERK activation by all three short stimulations, while ~30% cells started responding either after the second or the third one. All cells restored to its low ERK level state within an average time of 15±6 minutes. Interestingly, later stimulation induced more cells to respond in a synchronized manner. These results show that we can precisely synchronize the ERK activation with specific frequency by a minimal duration of localized AC EF stimulation.

Lastly, we show that the phosphorylation site of EGFR is the target of ACEF to activate ERK. Since we can exclude the involvement of electroporation, pH change, ROS and Ca2+, and temperature fluctuations, how did AC EF induce the ERK activation? To determine the detailed mechanism, we systematically inhibited various elements of EGFR-ERK signaling pathway. The canonical EGF-Ras-ERK signaling pathway is initialized by the binding of EGF to the EGFR, which triggers the dimerization and phosphorylation of EGFR, leading to Raf-MEK-ERK signaling (FIG. 5A)[22, 23]. We first applied the MEK inhibitor, trametinib (0.5 μM, Selleck Biochemicals), to the cells when trying to activate ERK using either AC EF (FIG. 5C, left columns) or with EGF as comparison (FIG. 5C, right column). In both cases, we observed inhibition of the ERK activation. Similarly, the Raf inhibitor, sorafenib (20 μM, Biotang) also abolished ERK activation under both stimulation scenarios (FIG. 5D). In addition, several small molecule tyrosine kinase inhibitors (TKIs) that binds to the intracellular tyrosine kinase domain of the epidermal growth factor receptor family (ErbB) family of receptors, including the irreversible pan-ErbB inhibitor, afatinib (5 μM, Selleck Biochemicals), which covalently binds to EGFR, HER2 and HER4[24], and the reversible EGFR selective inhibitors, erlotinib (2 μM, Selleckchem), and gefitinib (50 μM, Selleckchem)[24], was tested respectively. In all cases, the ERK activities were silenced under EF stimulation (FIG. 5E-5G, respectively). Surprisingly, however, when EGFR antibody cetuximab (100 μg/mL, ERBITUX) was used just to block the extracellular EGF binding site to the EGFR but leave the phosphorylation site intact, the AC EF could still activate ERK, although with an overall reduced contrast in the fluorescent signals (FIG. 5H). These were in sharp contrast to the tests with EGF stimulation controls where both TKIs and EGF antibody blocked ERK activation by EGF stimulations (control groups in FIG. 5B-5H). The time evolution of the ERKTR ratios in all blocker tests under EF stimulation are summarized in FIG. 5I, where we can see that the only trace showing ERK activation other than the blank control was the case where EGFR antibody were applied. We also note that for EGF antibody tests, a small retardation in time was often observed. The heat maps of the ERKTR ratio from all recorded cells are summarized in FIGS. 19A-19G. These results strongly suggest that the coupling between EF and ERK specifically followed the EGFR-Ras-ERK signaling pathway, initialized by EF-induced EGF-independent kinase activity of EGFR.

Precise modulations of the magnitude and the frequency/duration of ERK activity are fundamentally significant as both can impact the physiological outcome of ERK signaling in subtle, yet critical ways[1, 8, 25, 26]. Compared to chemical methods that usually have poor control in temporal and spatial resolution, our result of AC EF activation of ERK has its unique advantages as the spatial distribution and timing of FT can be engineered to accurately localize and synchronize events at the single-cell level. We have shown that AC EF can induce synchronized ERK activation under continuous stimulation (FIGS. 2A-2E and 3A-3C), and more importantly, provide precise control of ERK dynamics (FIGS. 4A-4C). It is therefore possible to accurately modulate the location, time, frequency, amplitude and duration of ERK activities by localized AC EF, without the requirement of genetic manipulation as in the case of optogenetics[14], or addition and washout of chemicals[8].

To date, investigations on how external EF couples with the ERK signaling pathways have all been focused either on direct-current (DC) and low frequency EF (several hundred Hz), or fast nanosecond pulses and high frequency radiations (several GHz). For example, Wolf-Goldberg et al showed that low frequency unipolar EF pulses (~500 Hz) applied through bare Pt electrodes in solution can cause ligand-independent activation of epidermal growth factor (EGF) receptor (EGFR), leading to ERK activation[19], where the pH changes and ROS due to electrochemical process at the electrode interface were identified as the possible cause. In addition, nanosecond pulses have been shown to activate p38, c-Jun N-terminal kinase (JNK) and ERK signaling pathways[27, 28], which was attributed to cell membrane electroporation and cytosolic Ca2+ level changes due to the EF stimulation. Furthermore, Sheikh et al. showed that microvascular endothelial cells that were exposed to 24 hours of high frequency EF (7.5 GHz) demonstrated enhanced ERK phosphorylation, among several other processes, where cRaf/MEK and Ca2+ pathways were involved.

Several major differences between our study and existing approaches should be highlighted. First, we used bipolar symmetric EF pulses with high-k dielectric passivated electrodes designed to eliminate Faradaic processes. This avoids possible biochemical complications and possible detrimental effects known that can happen to living cells and tissues with other techniques, where DC, unipolar or asymmetric EF were typically coupled to the cells through a low impedance metal interface in direct contact with the medium. We have, for the first time, clarified that intermediate ion flows and chemical species generated by electrochemical processes are not required for EF coupling with ERK signaling pathway. Second, no strong perturbation of the cell integrity was observed in our experiments (see Materials and Methods) due to the low EF strength, and the main frequency component of the EF (~50 kHz) falls in a middle range that has not been investigated before. Third, we have identified that AC EF can induce EGF-independent phosphorylation of EGFR which triggers the ERK signaling pathway. Although ligand-independent EGFR phosphorylation has been observed previously with bias applied through low-impedance Pt electrodes in contact with the medium, where ROS and decrease in pH were found to be the cause[19], however, here we have shown that no electrochemical processes are involved in our study.

Figure 20A:
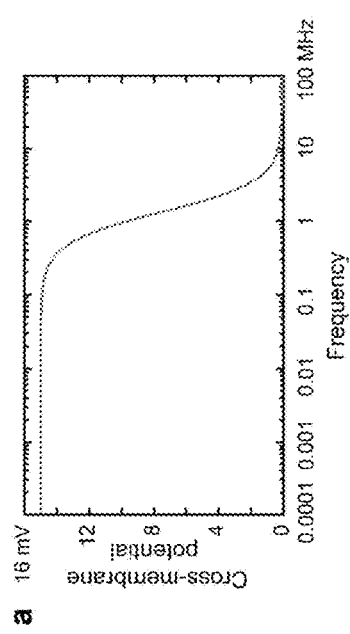
FIGS. 20A-20C. Estimation of cross-membrane potential for different AC EF frequencies applied at the electrodes, assuming cells are round and suspended in homogeneous medium (see text in section "Estimation of cross-membrane potential at different AC EF frequencies").
Figure 20B:
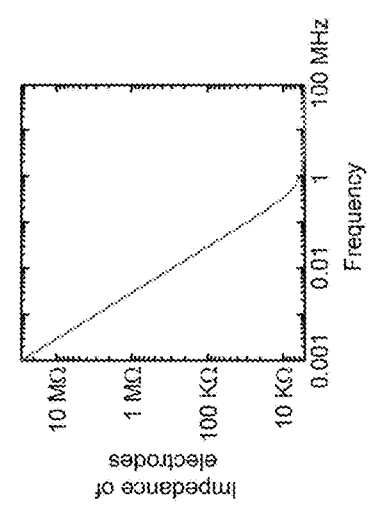
Figure 20C:
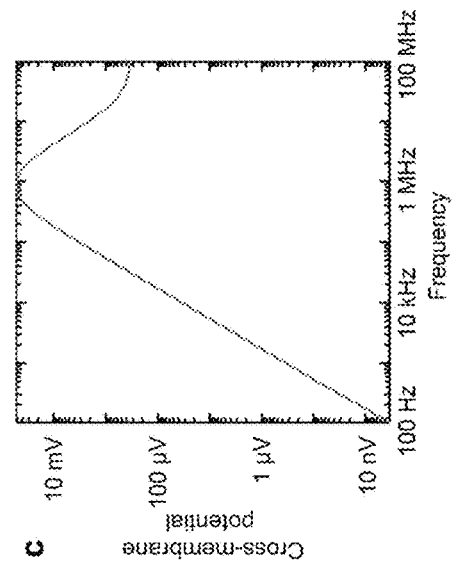
Figure 21A:
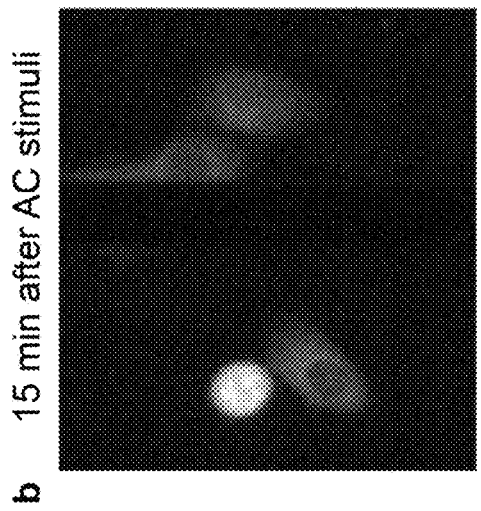
FIGS. 21A-21C. ERK activation by AC EF stimulation at low cell density. Fluorescence signals of cells that are not in contact with each other.
Figure 21B:
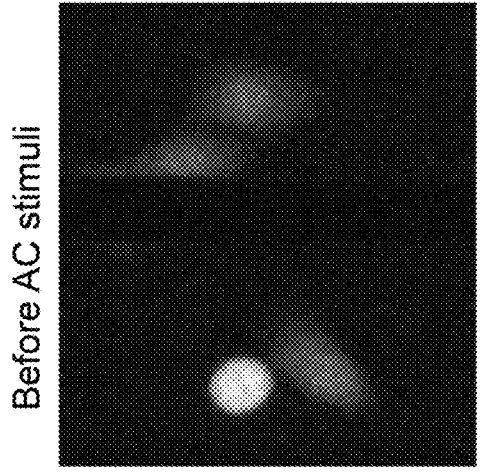
Figure 21C:
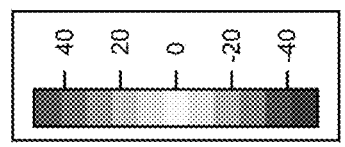
Figure 21C:
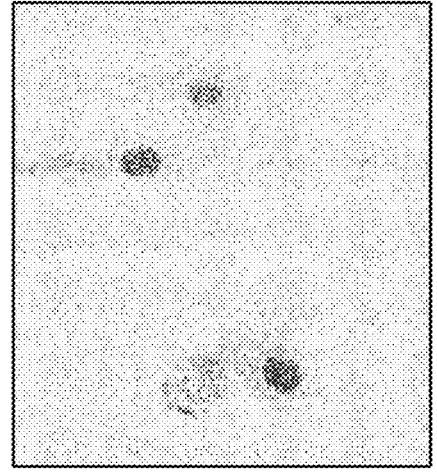

Using oscillating EF to tune membrane protein activities has been studied in Na—K pumps systems[29]. Specifically, it has been shown that when the frequency of the external EF matches the natural pumping rates of Na—K pumps (~50 Hz), individual pumps with initially different pumping rates and random pumping phases can be synchronized to generate enhanced transepithelial potential (TEP), due to field-induced energy changes in the ion-transports. However, in our case, the EGFR is not electrogenic and should not be sensitive to ion gradients, and the time scale of the EF pulses (10-20 µs) is obviously much faster in comparison to the operation time of ion pumps. More importantly, the comparison between AC-EF induced and EGF-induced ERK activation in our blocker tests (FIGS. 5A-5I) revealed an intriguing difference, that the extracellular EGFR antibody could only block the EGF stimulation but not the AC EF. This indicates that the AC EF could directly induce the EGFR phosphorylation without requiring EGF binding. To our knowledge, those results are the first demonstration of such unusual possibility, in addition to cases where EGFR can be "transactivated" through ligands binding to other receptors[30]. Our data suggest that there could be a new type of direct interaction between AC EF in this frequency range and membrane proteins such as EGFR. A possible explanation is that the spatial distribution of AC EF can be concentrated across the membrane of live cells in a frequency-dependent manner, which could modulate electrostatic interactions at the right time scale in favor of functional conformation changes of proteins[31]. We estimated the transient transmembrane voltage during one half phase of the AC EF to be between 0.1-16 mV (See FIGS. 20A-20C), which is consistent with the calculations by Taghian etc.[32]. While this might potentially bring physiological response from the cells, we note that our AC EF is completely symmetrical around 0 V with very fast switching time of 20 µs. And the whole process of AC EF activation of ERK signaling pathways is as short as 3-20 minutes. It is unlikely that what we observe is a response to membrane potential, which typically happens in a much longer time scale[33]. In addition, we have not observed appreciable difference in terms of threshold and timing of ERK response to the AC ET stimulation for low density of cells where individual cells are not in contact with each other (See FIGS. 21A-21C). Therefore, we suggest the observed ERK activation is more likely to be related to a rather fast dynamic process at the cell membrane induced by the AC EF. The detailed molecular mechanism of the specific phosphorylation of EGFR by external AC EF as first demonstrated here still need further investigation and modeling.

In summary, we have demonstrated non-invasive and highly localized technique to precisely control ERK activation dynamics by bipolar AC EF pulses applied through microelectrodes with no Faradaic processes involved. ERK activity in multiple cells can be reproducibly synchronized and modulated in time. The ERK activation seemed to be specifically initiated by EF induced EGF-independent phosphorylation of EGFR, and does not involve changes in pH, Ca2+ or ROS. Our work can serve as a unique platform for precise modulation of ERK activities and possibly other signaling pathways, and can find wide biomedical applications to control cell behaviors through modulating signaling dynamics which is difficult to achieve otherwise.

REFERENCES CITED HEREIN

1. Albeck, J. G.; Mills, G. B.; Brugge, J. S. Mol Cell 2013, 49, (2), 249-61.
2. Luciano, F.; Jacquel, A.; Colosetti, P.; Herrant, M.; Cagnol, S.; Pages, G.; Auberger, P. Oncogene 2003, 22, (43), 6785-93.
3. Allan, L. A.; Morrice, N.; Brady, S.; Magee, G.; Pathak, S.; Clarke, P. R. Nature cell biology 2003, 5, (7), 647-54.
4. Klemke, R. L; Cai, S.; Giannini, A. L.; Gallagher, P. J.; de Lanerolle, P.; Cheresh, D. A. J Cell Biol 1997, 137, (2), 481-92.
5. Lai, C. F.; Chaudhary, L.; Fausto, A.; Halstead, L. R.; Ory, D. S.; Avioli, L. V.; Cheng, S. L. J Biol Chem 2001, 276, (17), 14443-50.
6. Roux, P. P.; Blenis, J. Microbiol Mol Biol Rev 2004, 68, (2), 320-44.
7. Wortzel, I.; Seger, R. Genes Cancer 2011, 2, (3), 195-209.
8. Ryu, H.; Chung, M.; Dobrzynski, M.; Fey, D.; Blum, Y.; Lee, S. S.; Peter, M.; Kholodenko, B. N.; Jeon, N. L.; Peitz, O. Mol Syst Biol 2015, 11, (11), 838.
9. von Kriegsheim, A.; Baiocchi, D.; Birtwistle, M.; Sumpton, D.; Bienvenut, W.; Morrice, N.; Yamada, K.; Lamond, A.; Kalna, G.; Orton, R.; Gilbert, D.; Kolch, W. Nature cell biology 2009, 11, (12), 1458-64,
10. Lu, H.; Liu, S.; Zhang, G.; Bin, W.; Zhu, Y.; Frederick, D. T.; Hu, Y; Zhong, W.; Randell, S.; Sadek, N.; Zhang, W.; Chen, G.; Cheng, C.; Zeng, J.; Wu, L. W.; Zhang, J.; Liu, X.; Xu, W.; Krepler, C.; Sproesser, K.; Xiao, M.; Miao, B.; Liu, J.; Song, C. D.; Liu, J. Y.; Karakousis, G. C.; Schuchter, L. M.; Lu, Y.; Mills, G.; Cong, Y.; Chernoff, J.; Guo, J.; Boland, G. M.; Sullivan, R. J.; Wei, Z.; Field, J.; Amaravadi, R. K.; Flaherty, K. T.; Merlyn, M.; Xu, X.; Guo, W. Nature 2017, 550, (7674), 133-136.
11. Banks, A. S.; McAllister, F. E.; Camporez, J. P. G.; Zushin, P. J. H.; Jurczak, M. J.; Laznik-Bogosiayski, D.; Shulman, G. I.; Gygi, S. P.; Spiegelman, B. M. Nature 2015, 517, (7534), 391-U581.
12. Hiratsuka, T.; Fujita., Y.; Naoki, H.; Aoki, K.; Kamioka, Y.; Matsuda, M. Elite 2015, 4, e05178,
13. de la Cova, C.; Townley, R.; Regot, S.; Greenwald, I. Dev Cell 2017, 42, (5), 542-553 e4.
14. Toettcher, J. E.; Weiner, O. D.; Lim, W. A. Cell 2013, 155, (6), 1422-34.
15. Shankaran, H.; Ippolito, D. L.; Christer, W. B.; Resat, H.; Bollinger, N.; Opresko, L. K.; Wiley, H. S. Mol Syst Biol 2009, 5, 332.
16. Regot, S.; Hughey, J. J.; Bajar, B. T.; Carrasco, S.; Covert, M. W. Cell 2014, 157, (7), 1724-34.
17. Sparta, B.; Pargett, M.; Minguet, M.; Distor, K.; Bell, G.; Albeck, J. G. J Biol Chem 2015, 290, (41), 24784-92.
18. Subramaniam, S.; Zirrgiebel, U.; von Bohlen Und Halbach, O.; Strelau, J.; Laliberte, C.; Kaplan, D. R.; Unsicker, K. J Cell Biol 2004, 165, (3), 357-69.
19. Wolf-Goldberg, T.; Barbul, A.; Ben-Dov, N.; Korenstein, R. Biochim Biophys Acta 2013, 1833, (6), 1396-408.
20. Jura, N.; Endres, N. F.; Engel, K.; Deindl, S.; Das, R.; Lamers, M. H.; Wemmer, D. F.; Zhang, X.; Kuriyan, J. Cell 2009, 137, (7), 1293-307.
21. Yao, J.; Liu. B.; Qin, F. Biophys J 2009, 96, (9), 3611-9.
22. McKay, M. M.; Morrison, D. K. Oncogene 2007, 26, (22), 3113-21.
23. Oda, K.; Matsuoka, Y.; Funahashi, A.; Kitano, H. Mol Syst Biol 2005, 1, 2005 0010.
24. Modjtahedi, H.; Cho, B. C.; Michel, M. C.; Solca, F. Naunyn Schmiedebergs Arch Pharmacol 2014, 387, (6), 505-21.

25. Stork, P. J. Cell Cycle 2002, 1, (5), 315-7.
26. Murphy, L. O.; Smith, S.; Chen, R. H.; Fingar, D. C.; Blenis, J. Nature cell biology 2002, 4, (8), 556-64.
27. Morotomi-Yano, K.; Akiyama, Yano, K. Arch Biochem Biophys 2011, 515, (1-2), 99-106.
28. Semenov, I.; Xiao, S.; Pakhomov, A. G. Biochim Biophys Acta 2013, 1828, (3), 981-9.
29. Clausell, M.; Fang, Z.; Chen, W. J Membr Biol 2014, 247, (7), 601-9.
30. Rodland, K. D.; Bollinger, N.; Ippolito, D.; Opresko, L. K.; Coffey, R. J.; Zangar, R.; Wiley, H. S. J Biol Chem 2008, 283, (46), 31477-87.
31. McLaughlin, S.; Smith, S. O.; Hayman, M. J.; Murray, D. J Gen Physiol 2005, 126, (1), 41-53.
32. Taghian, T.; Narmoneva, D. A.; Kogan, A. B. J R Soc Interface 2015, 12, (107).
33. Levin, M.; Stevenson, C. G. Annual review of biomedical engineering 2012, 14, 295-323.

While this disclosure has been described with an emphasis upon particular embodiments, it will be obvious to those of ordinary skill in the art that variations of the particular embodiments may be used, and it is intended that the disclosure may be practiced otherwise than as specifically described herein. Features, characteristics, compounds, or examples described in conjunction with a particular aspect, embodiment, or example of the invention are to be understood to be applicable to any other aspect, embodiment, or example of the invention. Accordingly, this disclosure includes all modifications encompassed within the spirit and scope of the disclosure as defined by the following claims. We therefore claim as our invention all that comes within the scope and spirit of these claims.

We claim:

1. A method for activating a cell signaling pathway of interest in a cell, comprising:
   applying a time-modulated alternating current electrical field to the cell without occurrence of Faradaic processes, wherein the amplitude and frequency of the time-modulated alternating current electrical field are selected to activate the cell signaling pathway of interest, thereby activating the cell signaling pathway; and
   selecting a shape and/or timing of the time-modulated alternating current electrical field to activate the cell signaling pathway of interest in a selected population of cells,
   wherein the cell signaling pathway of interest comprises an ERK signaling pathway, and the time-modulated alternating current electrical field is applied by a pair of electrodes such that the ERK signaling pathway is activated in more than 80% of cells within a range of 50 μm from the pair of electrodes, and in less than 20% of cells within a range of greater than 100 μm from the pair of electrodes.

2. A method for activating a cell signaling pathway of interest in a cell, comprising:
   applying a time-modulated alternating current electrical field to the cell, wherein the amplitude and frequency of the time-modulated alternating current electrical field are selected to activate the cell signaling pathway of interest, thereby activating the cell signaling pathway, the frequency of the time-modulated alternating current electrical field being selected to be less than 100 kHz,
   wherein the cell signaling pathway of interest comprises an ERK signaling pathway.

3. The method of claim 2, wherein the time-modulated alternating current electrical field is applied to the cell without occurrence of Faradaic processes.

4. The method of claim 3, further comprising selecting a shape and/or timing of the time-modulated alternating current electrical field to activate the cell signaling pathway of interest in a selected population of cells.

5. The method of claim 3, wherein the time-modulated alternating current electrical field when applied does not cause a net ion current, or electroporation.

6. The method of claim 3, wherein the activation results in a post-translational modification of a signaling protein in the cell signaling pathway of interest.

7. The method of claim 3, wherein the amplitude and frequency of the time-modulated alternating current electrical field are selected to cause EGFR phosphorylation in the absence of EGF binding.

8. The method of claim 3, wherein the time-modulated alternating current electrical field is applied with surface microelectrode pairs.

9. The method of claim 8, wherein the microelectrode pairs are dielectric passivated microelectrodes.

10. The method of claim 8, wherein the surface of the microelectrode pairs includes a surface coating of $HfO_2$, $ZrO_2$, $Al_2O_3$, $SiO_2$, $TiO_2$, $Ta_2O_5$, $La_2O_3$, $Pr_2O_3$, $CrO_2$ or a combination thereof.

11. The method of claim 8, wherein the surface of the microelectrode pairs includes a surface coating of $HfO_2$.

12. The method of claim 3, wherein a shape of the time-modulated alternating current electrical field is selected from square wave, sine wave, triangle wave, and sawtooth wave or combinations thereof, combined with or without a silence interval time between pulses.

13. The method of claim 12, wherein a timing of each pulse phase of the time-modulated alternating current electrical field is between about 200 nanosecond and about 2 milliseconds.

14. The method of claim 12, wherein a timing of the silence interval time between each pulse is between 0 to 2 millisecond.

15. The method of claim 3, wherein the time-modulated alternating current electrical field is selected so that when applied it does not cause a net ion current, nor cause electroporation of a cell membrane of the cell.

16. The method of claim 3, wherein the time-modulated alternating current electrical field is applied with electrodes, and
   wherein an amplitude of an alternating current bias delivered to the electrodes is between about 0.1 V to about 10 V.

17. The method of claim 3, wherein the time-modulated alternating current electrical field is delivered continuously during a time interval having a duration within a range of about 15 minutes to about 2 hours.

18. The method of claim 3, wherein the time-modulated alternating current electrical field is delivered in repeated cycles between an active period of about 1 minute to about 30 minutes, and a silent period of about 10 minutes to about 60 minutes.

19. The method of claim 2, wherein the time-modulated alternating current electrical field is applied to the cell by a pair of electrodes, wherein an electrode of the pair of electrodes includes a passivating dielectric layer on its surface.

20. The method of claim 19, wherein the electrode of the pair of electrodes including the passivating dielectric layer on its surface is capacitively coupled to tissue including the cell.

\* \* \* \* \*